(12) United States Patent
Hastings et al.

(10) Patent No.: US 6,398,708 B1
(45) Date of Patent: *Jun. 4, 2002

(54) PERFUSION BALLOON AND RADIOACTIVE WIRE DELIVERY SYSTEM

(75) Inventors: Roger N. Hastings, Maple Grove; Michael J. Urick, Rogers, both of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/181,111

(22) Filed: Oct. 28, 1998

Related U.S. Application Data

(63) Continuation of application No. 08/868,482, filed on Jun. 3, 1997, now Pat. No. 5,855,546, which is a continuation-in-part of application No. 08/812,248, filed on Mar. 6, 1997, now Pat. No. 6,099,454, which is a continuation-in-part of application No. 08/782,471, filed on Jan. 10, 1997, now Pat. No. 6,234,951, which is a continuation-in-part of application No. 08/608,655, filed on Feb. 29, 1996, now Pat. No. 5,882,290.

(51) Int. Cl.[7] .................................................. A61N 5/00

(52) U.S. Cl. ............................................. 600/3; 604/96
(58) Field of Search ........................... 600/1–8; 604/93, 604/96, 102, 103

(56) References Cited

U.S. PATENT DOCUMENTS

| | | | |
|---|---|---|---|
| 2,546,761 A | 3/1951 | Loftus | 128/1.2 |
| 2,862,108 A | 11/1958 | Meilink | 250/106 |
| 2,955,208 A | 10/1960 | Stevens | 250/108 |
| 3,060,924 A | 10/1962 | Rush | 128/1.2 |

(List continued on next page.)

FOREIGN PATENT DOCUMENTS

| | | |
|---|---|---|
| CA | 2166915 A | 8/1996 |
| DE | 91 02 312.2 | 8/1992 |
| DE | 195 26 680 A1 | 1/1997 |
| DE | 197 54 870 A1 | 8/1998 |
| DE | 197 24 233 C1 | 12/1998 |

(List continued on next page.)

OTHER PUBLICATIONS

Tjho–Heslinga et al., "Results of ruthenium irradiation of uveal melanona", *Radiotherapy Oncology*, vol. 29, pp. 33–38, 1993.

Lommatzsch et al., "Radiation effects on the optic nerve observed after brachytherapy of choroidal melanomas with 106 Ru/106 Rh plaques", *Graefe's Arch. Clin. Exp. Opthalmology* vol. 232, pp. 482–487, 1994.

*Radiotherapy of Intraoculare and Orbital Tumors*, Springer–Verlak publishers, Berlin Heidelberg and New York, copyright 1993, pp. 23–30 and 363–367.

(List continued on next page.)

*Primary Examiner*—John P. Lacyk
(74) *Attorney, Agent, or Firm*—Crompton, Seager & Tufte, LLC

(57) ABSTRACT

A catheter capable of irradiating blood vessel walls to inhibit restenosis after angioplasty. Catheters are capable of simultaneous irradiation, angioplasty, and in some devices, drug infusion. Preferred catheters include a helical perfusion balloon having strand windings spaced apart when inflated and defining a perfusion lumen within. A tubular sheath over the helical strands and distal shaft region is used in some embodiments and defines an outer wall for the perfusion lumen. A spiral, inter-strand space is defined between the sheath outer wall and the blood vessel inner wall, providing a confined volume for controlled delivery of drugs to the vessel wall in conjunction with irradiation. A device having a radiation wire, distally closed-end tube is provided. A device having a radiation wire open ended tube terminating proximally of the perfusion lumen is also provided.

18 Claims, 12 Drawing Sheets

U.S. PATENT DOCUMENTS

| | | | |
|---|---|---|---|
| 3,147,383 A | 9/1964 | Prest | 250/108 |
| 3,324,847 A | 6/1967 | Zoumboulis | 128/1.2 |
| 3,505,991 A | 4/1970 | Hellerstein et al. | 128/1.1 |
| 3,643,096 A | 2/1972 | Jeffries, Jr. et al. | 250/108 R |
| 3,669,093 A | 6/1972 | Sauerwein et al. | 128/1.1 |
| 3,674,006 A | 7/1972 | Holmer | 128/1.2 |
| 3,750,653 A | 8/1973 | Simon | 128/1.2 |
| 3,811,426 A | 5/1974 | Culver et al. | 128/1.2 |
| 3,861,380 A | 1/1975 | Chassagne et al. | 128/1.2 |
| 3,866,050 A | 2/1975 | Whifield | 250/497 |
| 3,927,325 A | 12/1975 | Hungate et al. | 250/435 |
| 4,096,862 A | 6/1978 | DeLuca | 128/348 |
| 4,220,864 A | 9/1980 | Sauerwein et al. | 250/497 |
| 4,225,790 A | 9/1980 | Parsons, Jr. et al. | 250/497 |
| 4,244,357 A | 1/1981 | Morrison | 128/1.2 |
| 4,281,252 A | 7/1981 | Parsons, Jr. et al. | 250/497 |
| 4,314,157 A | 2/1982 | Gaines | 250/497 |
| 4,364,376 A | 12/1982 | Bigham | 128/1.1 |
| 4,584,991 A | 4/1986 | Tokita et al. | 128/1.1 |
| 4,588,395 A | 5/1986 | Lemelson | 604/59 |
| 4,631,415 A | 12/1986 | Sauerwein et al. | 250/497.1 |
| 4,702,228 A | 10/1987 | Russell, Jr. et al. | 128/1.2 |
| 4,706,652 A | 11/1987 | Horowitz | 128/1.2 |
| 4,763,642 A | 8/1988 | Horowitz | 128/1.2 |
| 4,763,671 A | 8/1988 | Goffinet | 128/786 |
| 4,782,834 A | 11/1988 | Maguire et al. | 128/344 |
| 4,784,116 A | 11/1988 | Russell, Jr. et al. | 128/1.2 |
| 4,799,479 A | 1/1989 | Spears | 128/303.1 |
| 4,815,449 A | 3/1989 | Horowitz | 600/7 |
| 4,819,618 A | 4/1989 | Liprie | 600/7 |
| 4,851,694 A | 7/1989 | Rague et al. | 250/497.1 |
| 4,861,520 A | 8/1989 | van't Hooft et al. | 252/644 |
| 4,881,937 A | 11/1989 | van't Hooft et al. | 600/3 |
| 4,897,076 A | 1/1990 | Puthawala et al. | 600/7 |
| 4,936,823 A | 6/1990 | Colvin et al. | 600/7 |
| 4,963,128 A | 10/1990 | Daniel et al. | 600/7 |
| 4,969,863 A | 11/1990 | van't Hooft et al. | 600/3 |
| 4,976,266 A | 12/1990 | Huffman et al. | 128/659 |
| 4,976,680 A | 12/1990 | Hayman et al. | 600/7 |
| 4,976,690 A | 12/1990 | Solar et al. | 604/96 |
| 5,030,194 A | 7/1991 | Van't Hooft | 600/3 |
| 5,032,113 A | 7/1991 | Burns | 604/96 |
| 5,059,166 A | 10/1991 | Fischell et al. | 600/3 |
| 5,084,001 A | 1/1992 | Van't Hooft et al. | 600/3 |
| 5,084,002 A | 1/1992 | Liprie | 600/7 |
| 5,092,834 A | 3/1992 | Bradshaw et al. | 600/7 |
| 5,103,395 A | 4/1992 | Spako et al. | 364/413.26 |
| 5,106,360 A | 4/1992 | Ishiwara et al. | 600/2 |
| 5,120,973 A | 6/1992 | Rohe et al. | 250/497.1 |
| 5,139,473 A | 8/1992 | Bradshaw et al. | 600/3 |
| 5,141,487 A | 8/1992 | Liprie | 600/7 |
| 5,147,282 A | 9/1992 | Kan | 600/1 |
| 5,163,896 A | 11/1992 | Suthanthiran et al. | 600/8 |
| 5,176,617 A | 1/1993 | Fischell et al. | 600/3 |
| 5,183,455 A | 2/1993 | Hayman et al. | 600/7 |
| 5,199,939 A | 4/1993 | Dake et al. | 600/3 |
| 5,213,561 A | 5/1993 | Weinstein et al. | 600/7 |
| 5,267,960 A | 12/1993 | Hayman et al. | 604/106 |
| 5,282,781 A | 2/1994 | Liprie | 600/3 |
| 5,302,168 A * | 4/1994 | Hess | 600/3 |
| 5,308,356 A | 5/1994 | Blackshear, Jr. et al. | 606/94 |
| 5,344,383 A | 9/1994 | Liping | 600/3 |
| 5,354,257 A | 10/1994 | Roubin et al. | 600/7 |
| 5,370,685 A | 12/1994 | Stevens | 623/2 |
| 5,391,139 A | 2/1995 | Edmundson | 600/7 |
| 5,395,300 A | 3/1995 | Liprie | 600/3 |
| 5,405,309 A | 4/1995 | Carden, Jr. | 600/3 |
| 5,409,015 A | 4/1995 | Palermo | 128/772 |
| 5,411,466 A | 5/1995 | Hess | 600/3 |
| 5,417,653 A | 5/1995 | Sahota et al. | 604/20 |
| 5,425,720 A | 6/1995 | Rogalsky et al. | 604/198 |
| 5,429,582 A | 7/1995 | Williams | 600/2 |
| 5,484,384 A | 1/1996 | Fearnot | 600/3 |
| 5,498,227 A | 3/1996 | Mawad | 600/3 |
| 5,503,613 A | 4/1996 | Weinberger | 600/3 |
| 5,503,614 A | 4/1996 | Liprie | 600/7 |
| 5,532,122 A | 7/1996 | Drukier | 435/5 |
| 5,538,494 A | 7/1996 | Matsuda | 600/1 |
| 5,540,659 A | 7/1996 | Teirstein | 604/104 |
| 5,545,132 A | 8/1996 | Fagan et al. | 604/96 |
| 5,556,389 A | 9/1996 | Liprie | 604/264 |
| 5,558,642 A | 9/1996 | Schweich, Jr. et al. | 604/96 |
| 5,575,749 A | 11/1996 | Liprie | 600/3 |
| 5,605,530 A | 2/1997 | Fischell et al. | 600/3 |
| 5,611,767 A | 3/1997 | Williams | 600/2 |
| 5,616,114 A | 4/1997 | Thornton et al. | 600/3 |
| 5,618,266 A | 4/1997 | Liprie | 604/21 |
| 5,624,372 A | 4/1997 | Liprie | 604/3 |
| 5,643,171 A | 7/1997 | Bradshaw et al. | 600/1 |
| 5,649,924 A | 7/1997 | Everett et al. | 606/15 |
| 5,653,683 A | 8/1997 | D'Andrea | 604/21 |
| 5,662,580 A | 9/1997 | Bradshaw et al. | 600/3 |
| 5,674,177 A | 10/1997 | Hehrlein et al. | 600/3 |
| 5,683,345 A | 11/1997 | Waksman et al. | 600/3 |
| 5,688,220 A | 11/1997 | Verin et al. | 600/1 |
| 5,707,332 A | 1/1998 | Weinberger | 600/3 |
| 5,713,828 A | 2/1998 | Coniglione | 600/7 |
| 5,720,717 A | 2/1998 | D'Andrea | 604/21 |
| 5,722,984 A | 3/1998 | Fischell et al. | 606/198 |
| 5,728,042 A | 3/1998 | Schwager | 600/3 |
| 5,730,698 A | 3/1998 | Fischell et al. | 600/3 |
| 5,782,740 A | 7/1998 | Schneiderman | 600/1 |
| 5,782,742 A | 7/1998 | Crocker et al. | 600/3 |
| 5,795,286 A | 8/1998 | Fischell et al. | 600/3 |
| 5,800,333 A | 9/1998 | Liprie | 600/3 |
| 5,803,895 A | 9/1998 | Kronholz et al. | 600/3 |
| 5,807,231 A | 9/1998 | Liprie | 600/3 |
| 5,816,259 A | 10/1998 | Rose | 128/898 |
| 5,816,999 A | 10/1998 | Bischoff et al. | 600/3 |
| 5,820,553 A | 10/1998 | Hughes | 600/426 |
| 5,833,593 A | 11/1998 | Liprie | 600/3 |
| 5,840,008 A | 11/1998 | Klein et al. | 600/3 |
| 5,840,009 A | 11/1998 | Fischell et al. | 600/3 |
| 5,840,064 A | 11/1998 | Liprie | 604/96 |
| 5,843,163 A | 12/1998 | Wall | 623/1 |
| 5,851,171 A | 12/1998 | Gasson | 600/3 |
| 5,851,172 A | 12/1998 | Bueche et al. | 600/7 |
| 5,855,546 A | 1/1999 | Hastings et al. | 600/3 |
| 5,857,956 A | 1/1999 | Liprie | 600/7 |
| 5,863,284 A | 1/1999 | Klein | 600/3 |
| 5,863,285 A | 1/1999 | Coletti | 600/3 |
| 5,865,720 A | 2/1999 | Hastings et al. | 600/3 |
| 5,871,436 A | 2/1999 | Eury | 600/3 |
| 5,871,437 A | 2/1999 | Alt | 600/3 |
| 5,873,811 A | 2/1999 | Wang et al. | 600/5 |
| 5,879,282 A | 3/1999 | Fischell et al. | 600/3 |
| 5,882,290 A | 3/1999 | Kume | 600/3 |
| 5,882,291 A | 3/1999 | Bradshaw et al. | 600/3 |
| 5,891,091 A | 4/1999 | Teirstein | 604/104 |
| 5,897,573 A | 4/1999 | Rosenthal et al. | 606/224 |
| 5,899,882 A | 5/1999 | Waksman et al. | 604/96 |
| 5,906,573 A | 5/1999 | Aretz | 600/3 |
| 5,910,101 A | 6/1999 | Andrews et al. | 600/3 |
| 5,910,102 A | 6/1999 | Hastings | 600/3 |
| 5,913,813 A | 6/1999 | Williams et al. | 600/3 |
| 5,916,143 A | 6/1999 | Apple et al. | 600/3 |
| 5,919,126 A | 7/1999 | Armini | 600/3 |
| 5,924,973 A | 7/1999 | Weinberger | 600/3 |
| 5,924,974 A | 7/1999 | Loffler | 600/3 |
| 5,938,582 A | 8/1999 | Ciamacco, Jr. et al. | 600/3 |

| | | | | | | |
|---|---|---|---|---|---|---|
| 5,947,899 A | 9/1999 | Hehrlein .................... 600/3 | WO | WO 98/11936 | 3/1998 | |
| 5,947,924 A | 9/1999 | Liprie ....................... 604/96 | WO | WO 98/16151 | 4/1998 | |
| 5,947,958 A | 9/1999 | Woodard et al. ........... 606/1.5 | WO | WO 98/20935 | 5/1998 | |
| 5,957,829 A | 9/1999 | Thornton .................... 600/3 | WO | WO 98/25674 | 6/1998 | |
| 5,961,439 A | 10/1999 | Chernomorsky et al. ...... 600/4 | WO | WO 98/29049 | 7/1998 | |
| 5,967,966 A | 10/1999 | Kronholz et al. ............. 600/3 | WO | WO 98/30273 | 7/1998 | |
| 5,971,909 A | 10/1999 | Bradshaw et al. ............ 600/3 | WO | WO 98/34681 | 8/1998 | |
| 5,976,106 A | 11/1999 | Verin et al. .................. 604/96 | WO | WO 98/36788 | 8/1998 | |
| 5,997,462 A | 12/1999 | Loffler ........................ 600/3 | WO | WO 98/36790 | 8/1998 | |
| 5,997,463 A | 12/1999 | Cutrer ......................... 600/8 | WO | WO 98/36796 | 8/1998 | |
| 6,010,445 A | 1/2000 | Armini et al. ................ 600/3 | WO | WO 98/39052 | 9/1998 | |
| 6,013,019 A | 1/2000 | Fischell et al. ............... 600/3 | WO | WO 98/39062 | 9/1998 | |
| 6,013,020 A | 1/2000 | Meloul et al. ................ 600/7 | WO | WO 98/39063 | 9/1998 | |
| 6,024,690 A | 2/2000 | Lee et al. ..................... 600/3 | WO | WO 98/40032 | 9/1998 | |
| 6,030,333 A | 2/2000 | Sioshansi et al. ............. 600/3 | WO | WO 98/46309 | 10/1998 | |
| 6,033,357 A | 3/2000 | Ciezki et al. ................. 600/3 | WO | WO 98/55179 | 12/1998 | |

FOREIGN PATENT DOCUMENTS

| | | |
|---|---|---|
| DE | 197 58 234 | 7/1999 |
| DE | 198 07 727 | 7/1999 |
| DE | 198 25 563 | 12/1999 |
| DE | 198 25 999 | 12/1999 |
| DE | 198 26 000 | 12/1999 |
| DE | 198 29 447 | 1/2000 |
| EP | 0 433 011 B1 | 6/1991 |
| EP | 0 497 495 A2 | 8/1992 |
| EP | 0 514 913 A2 | 11/1992 |
| EP | 0 633 041 A1 | 1/1995 |
| EP | 0 686 342 A1 | 12/1995 |
| EP | 0 688 580 A1 | 12/1995 |
| EP | 0 696 906 B1 | 2/1996 |
| EP | 0 749 764 A1 | 12/1996 |
| EP | 0 754 472 A2 | 1/1997 |
| EP | 0 754 473 A2 | 1/1997 |
| EP | 0 778 051 A1 | 6/1997 |
| EP | 0 801 961 A2 | 10/1997 |
| EP | 0 810 004 | 12/1997 |
| EP | 0 813 894 A2 | 12/1997 |
| EP | 0 593 136 B1 | 7/1998 |
| EP | 0 629 380 B1 | 7/1998 |
| EP | 0 865 803 | 9/1998 |
| EP | 0 904 798 | 3/1999 |
| EP | 0 904 799 | 3/1999 |
| JP | 10071210 | 3/1998 |
| WO | WO 86/03124 | 6/1986 |
| WO | WO 93/04735 | 3/1993 |
| WO | WO 94/25106 | 11/1994 |
| WO | WO 94/26205 | 11/1994 |
| WO | WO 95/07732 | 3/1995 |
| WO | WO 95/19807 | 7/1995 |
| WO | WO 95/26681 | 10/1995 |
| WO | WO 96/06654 | 3/1996 |
| WO | WO 96/10436 | 4/1996 |
| WO | WO 96/13303 | 5/1996 |
| WO | WO 96/14898 | 5/1996 |
| WO | WO 96/17654 | 6/1996 |
| WO | WO 96/22121 | 7/1996 |
| WO | WO 96/29943 | 10/1996 |
| WO | WO 96/40352 | 12/1996 |
| WO | WO 97/07740 | 3/1997 |
| WO | WO 97/09937 | 3/1997 |
| WO | WO 97/17029 | 5/1997 |
| WO | WO 97/18012 | 5/1997 |
| WO | WO 97/19706 | 6/1997 |
| WO | WO 97/25102 | 7/1997 |
| WO | WO 97/25103 | 7/1997 |
| WO | WO 97/40889 | 11/1997 |
| WO | WO 98/01183 | 1/1998 |
| WO | WO 98/01184 | 1/1998 |
| WO | WO 98/01185 | 1/1998 |
| WO | WO 98/01186 | 1/1998 |
| WO | WO 98/57706 | 12/1998 |
| WO | WO 98/01179 | 1/1999 |
| WO | WO 99/02219 | 1/1999 |
| WO | WO 99/04706 | 2/1999 |
| WO | WO 99/04856 | 2/1999 |
| WO | WO 99/10045 | 3/1999 |
| WO | WO 99/21615 | 5/1999 |
| WO | WO 99/21616 | 5/1999 |
| WO | WO 99/22774 | 5/1999 |
| WO | WO 99/22775 | 5/1999 |
| WO | WO 99/22812 | 5/1999 |
| WO | WO 99/22815 | 5/1999 |
| WO | WO 99/24116 | 5/1999 |
| WO | WO 99/24117 | 5/1999 |
| WO | WO 99/29354 | 6/1999 |
| WO | WO 99/29370 | 6/1999 |
| WO | WO 99/29371 | 6/1999 |
| WO | WO 99/30779 | 6/1999 |
| WO | WO 99/34969 | 7/1999 |
| WO | WO 99/36121 | 7/1999 |
| WO | WO 99/39628 | 8/1999 |
| WO | WO 99/40962 | 8/1999 |
| WO | WO 99/40970 | 8/1999 |
| WO | WO 99/40971 | 8/1999 |
| WO | WO 99/40972 | 8/1999 |
| WO | WO 99/40973 | 8/1999 |
| WO | WO 99/40974 | 8/1999 |
| WO | WO 99/42162 | 8/1999 |
| WO | WO 99/42163 | 8/1999 |
| WO | WO 99/42177 | 8/1999 |
| WO | WO 99/44686 | 9/1999 |
| WO | WO 99/44687 | 9/1999 |
| WO | WO 99/49935 | 10/1999 |
| WO | WO 99/56825 | 11/1999 |
| WO | WO 99/56828 | 11/1999 |
| WO | WO 99/61107 | 12/1999 |
| WO | WO 99/62598 | 12/1999 |
| WO | WO 99/66979 | 12/1999 |
| WO | WO 00/03292 | 1/2000 |
| WO | WO 00/04838 | 2/2000 |
| WO | WO 00/04953 | 2/2000 |
| WO | WO 00/09212 | 2/2000 |

OTHER PUBLICATIONS

Fackelmann, "Harbinger of a Heart Attack", *Science News*, vol. 151, Jun. 14, 1997, pp. 374–375.

Raloff, "Nuclear Medicine Gets Friendlier—Experimental Therapies Seek to Poison Just the Disease", *Science News*, Bol. 152, Jul. 19, 1997, pp. 40–41.

Li et al., "Reactive Oxygen Species Induce Apoptosis of the Vascular Smooth Muscle Cell", *FEBS Letters*, 404, 1997, pp. 249–252.

Kalli, Oxygen Emulsion The Question of Free Radicals:, Internet Address http:/www.livelinks.com/sumeria/oxy/rad2.html, Aug. 1, 1997.

Block, "Peroxygen Compounds, Chapter 9", *Disinfection, Sterilization, and Preservation*, Fourth Edition, Lea & Febiger, Philadelphia, Copyright 1991.

Moore, "Free Radial Generation by Thyroid Peroxidase and Its Effects on Cells in Vitro", PhD. Dissertation, Group in Endocrinology–University of California, Berkeley California, Dec. 1990.

Barry, "Reactive Oxygen Species in Living Systems—Gource: Biochemistry, and Roale in Human Disease", Internet Address http:/www.livelinks/sumeria/oxy/reactive.html, Jul. 21, 1997 from *American Journal of Medicine*, vol. 91, No. 3C, Sep. 30, 1991, p. 14S (9).

"Aids and Cancer Cured by Hyper–Oxygenation", *Now What*, Issue No. 1, 1987, Waves Forrest, Monterey, California.

Varma et al., Hydrogen Peroxide in Human Blood:, *Free Rad. Res. Comms.*, vol. 14, No. 2, pp. 125–131.

Nakayama et al., "Comparison of the Cytotoxicity of Different Hydroperoxides to V79 Cells", *Free Rad. Res. Comms.*, vol. 14, No. 3, pp. 173–178.

Sutherland, "Managing Cancer Through Synergy", *Administrative Radiology Journal*, Nov. 1996, pp. 21–27.

* cited by examiner

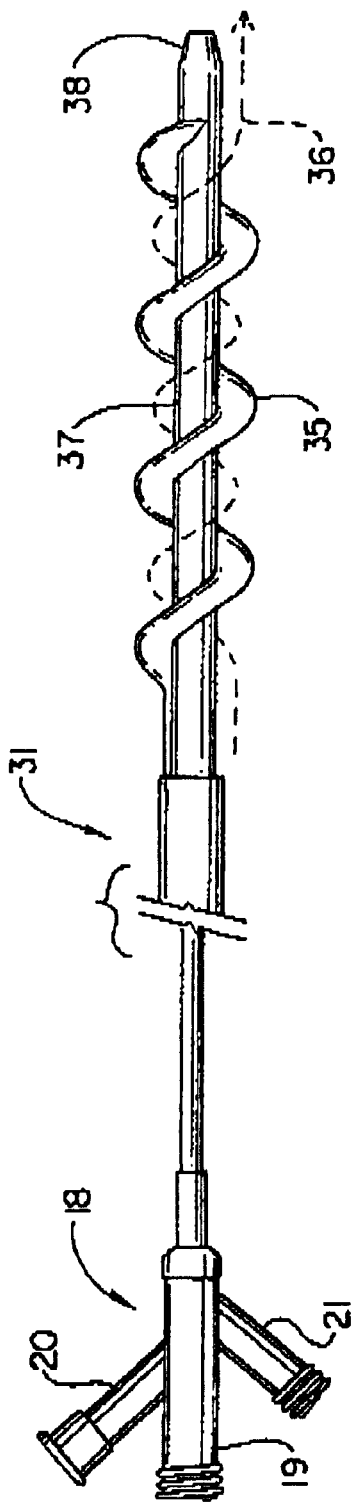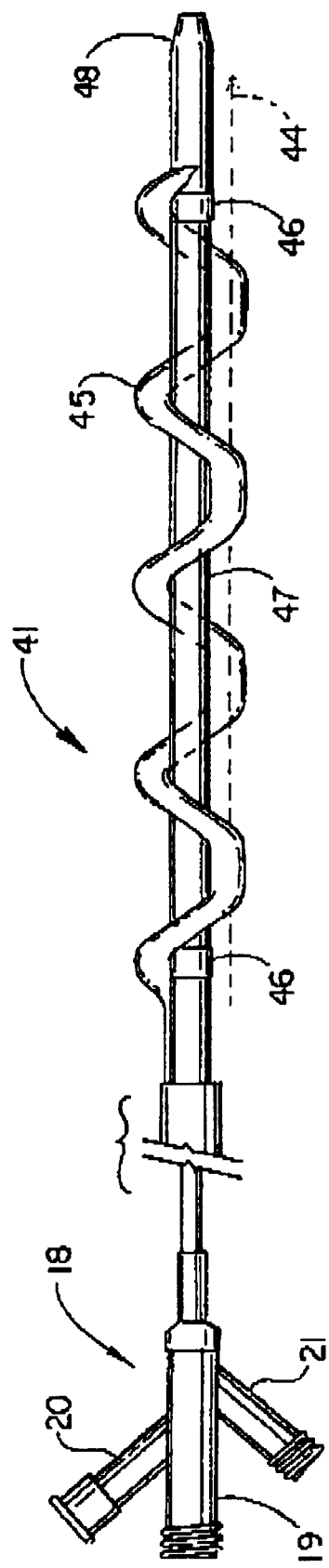

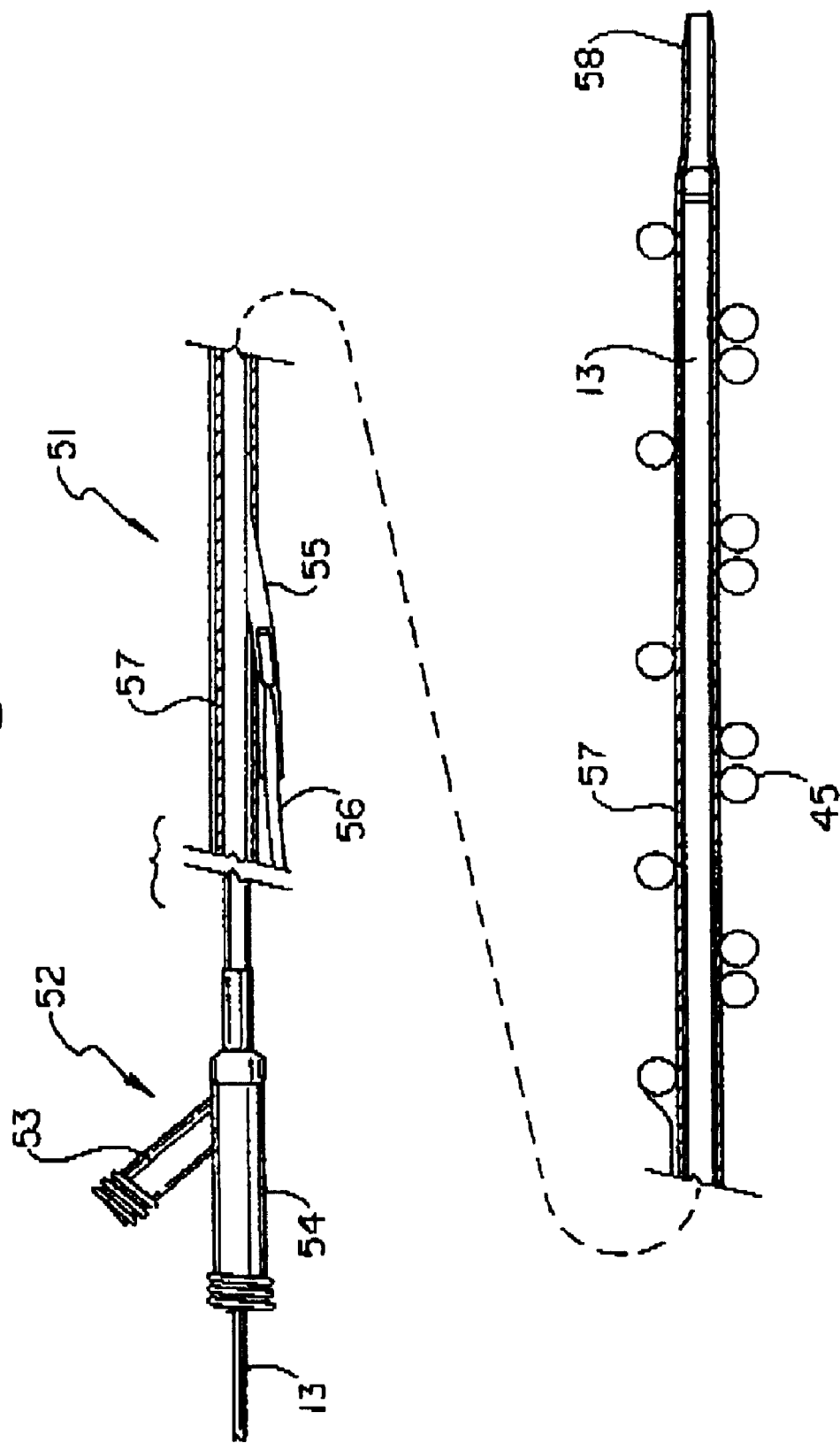

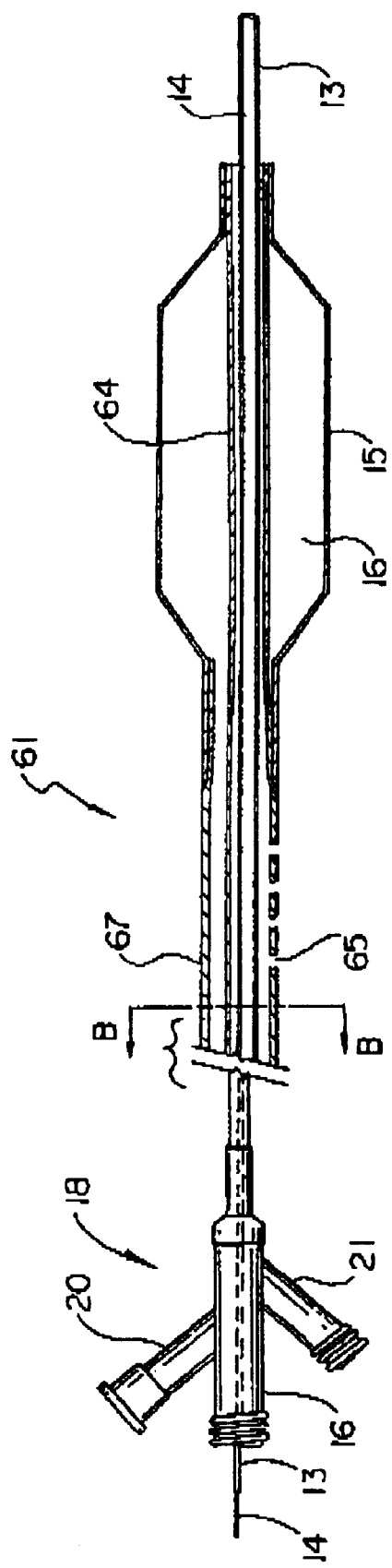

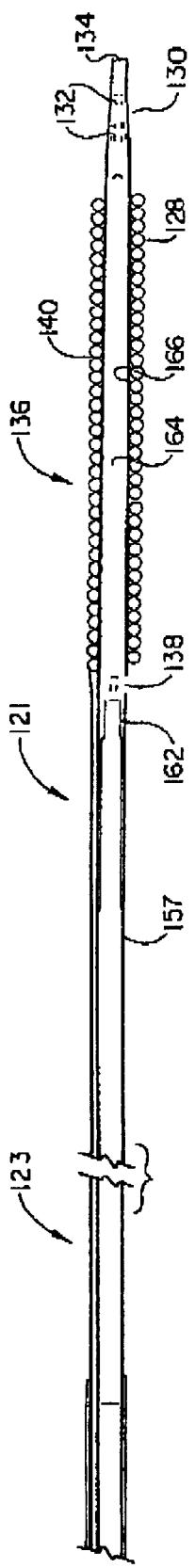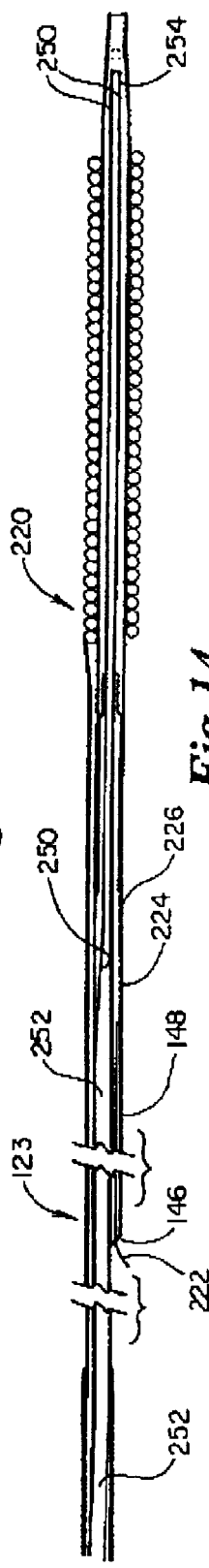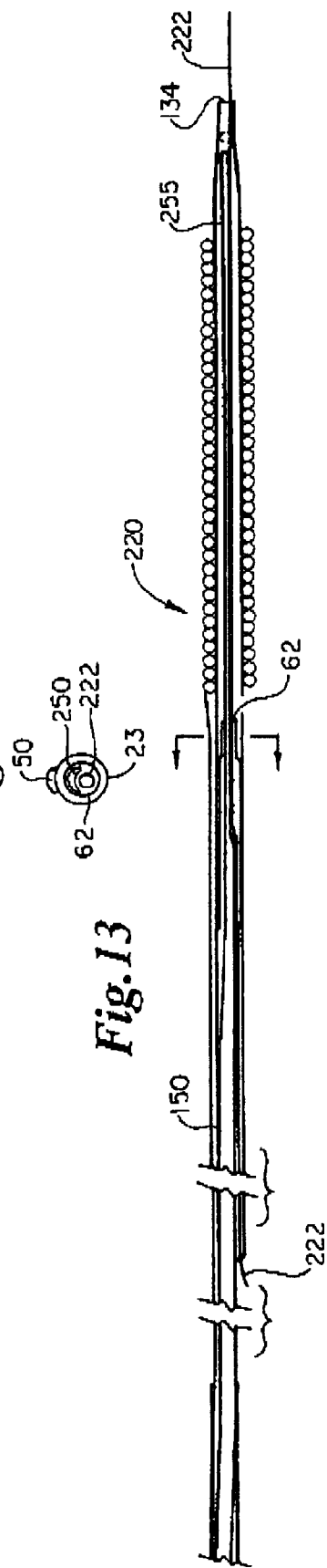

PERFUSION BALLOON AND RADIOACTIVE WIRE DELIVERY SYSTEM

CROSS-REFERENCE TO RELATED APPLICATIONS

This application is a continuation of application Ser. No. 08/868,482 filed Jun. 3, 1997 U.S. Pat. No. 5,855,546, which is a continuation-in-part of U.S. patent application Ser. No. 08/812,248, filed Mar. 6, 1997, entitled PERFUSION BALLOON AND RADIOACTIVE WIRE DELIVERY SYSTEM, now U.S. Pat. No. 6,099,454; which is a continuation-in-part of U.S. patent application Ser. No. 08/782,471, filed Jan. 10, 1997, entitled INTRAVASCULAR RADIATION DELIVERY SYSTEM, now U.S. Pat. No. 6,234,951; which is a continuation-in-part of U.S. patent application Ser. No. 08/608,655, filed Feb. 29, 1996, now U.S. Pat. No. 5,882,290; the entire disclosures of which are herein incorporated by reference. This application is related to U.S. Pat. No. 5,558,642, entitled DRUG DELIVERY CATHETER, also incorporated by reference.

FIELD OF THE INVENTION

The present invention relates generally to intralumenal or intravascular catheters used to delivery radiation inside a living body. More specifically, the present invention relates to radioactive perfusion balloon catheters for therapeutic purposes.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve use of a guide wire and a balloon catheter, possibly in combination with other intravascular devices. A typical balloon catheter has an elongate shaft with a balloon attached to its distal end and a manifold attached to the proximal end. In use, the balloon catheter is advanced over the guide wire such that the balloon is positioned adjacent a restriction in a diseased vessel. The balloon is then inflated and the restriction in the vessel is opened.

Vascular restrictions that have been dilated do not always remain open. In approximately 30% of the cases, a restriction reappears over a period of months. The mechanism of this restenosis is not understood. The mechanism is believed to be different from the mechanism that caused the original stenosis. It is believed that rapid proliferation of vascular smooth muscle cells surrounding the dilated region may be involved. Restenosis may be in part a healing response to the dilation, including the formation of scar tissue.

Drug infusion near the stenosis has been proposed as a means to inhibit restenosis. U.S. Pat. No. 5,558,642 to Schweich, Jr. et al. describes drug delivery devices and methods for delivering pharmacological agents to vessel walls in conjunction with angioplasty.

Intravascular radiation, including thermal, light and radioactive radiation, has been proposed as a means to prevent or reduce the effects of restenosis. For example, U.S. Pat. No. 4,799,479 to Spears suggests that heating a dilated restriction may prevent gradual restenosis at the dilation site. In addition, U.S. Pat. No. 5,417,653 to Sahota et al. suggests that delivering relatively low energy light, following dilatation of a stenosis, may inhibit restenosis. Furthermore, U.S. Pat. No. 5,199,939 to Dake et al. suggests that intravascular delivery of radioactive radiation may be used to prevent restenosis. While most clinical studies suggest that thermal radiation and light radiation are not significantly effective in reducing restenosis, some clinical studies have indicated that intravascular delivery of radioactive radiation is a promising solution to the restenosis enigma.

Since radiation prevents restenosis but will not dilate a stenosis, radiation is preferably administered during or after dilatation. European Pat. No. 0 688 580 to Verin discloses a device and method for simultaneously dilating a stenosis and delivering radioactive radiation. In particular, Verin discloses a balloon dilatation catheter having an open-ended lumen extending therethrough for the delivery of a radioactive guide wire.

One problem associated with the open-ended lumen design is that bodily fluids (e.g., blood) may come into contact with the radioactive guide wire. This may result in contamination of the guide wire bodily fluid and require the resterilization or disposal of the radioactive guide wire. To address these issues, U.S. Pat. No. 5,503,613 to Weinberger et al. proposes the use of a separate closed-ended lumen in a balloon catheter. The closed-ended lumen may be used to deliver a radioactive guide wire without the risk of contaminating the blood and without the need to resterilize or dispose of the radiation source.

The closed-ended lumen design also has draw backs. For example, the addition of a separate delivery lumen tends to increase the overall profile of the catheter. An increase in profile is not desirable because it may reduce flow rate of fluid injections into the guide catheter and it may interfere with navigation in small vessels.

Another problem with both the open-ended and closed-ended devices is that radiation must travel through the fluid filled balloon in order to reach the treatment site. While this is not a problem for gamma radiation, it poses a significant problem for beta radiation which does not penetrate as well as gamma radiation. Beta radiation is considered a good candidate for radiation treatment because it is easy to shield and control exposure. In larger vessels (e.g., 0.5 cm or larger), a fluid filled balloon absorbs a significant amount of beta radiation and severely limits exposure to the treatment site.

Other intravascular treatments, including delivery of radioactive radiation have been proposed as a means to prevent or reduce the effects of restenosis. Dake et al. suggest delivering radiation within the distal portion of a tubular catheter. Fischell, in the publication EPO 0 593 136 A1, suggests placing a thin wire having a radioactive tip near the site of vessel wall trauma for a limited time to prevent restenosis. Problems exist in attempting to provide uniform radiation exposure using a point or line source. Specifically, as the radiation varies inversely with the square of distance for a point source and inversely with distance for a line source laying off center near one vessel wall may significantly overexpose the nearby wall while underexposing the further away wall. This is especially critical for beta radiation which is absorbed by tissue and blood at a relatively short distance from the source.

Bradshaw, in PCT publication WO 94/25106, proposes using an inflatable balloon to center the radiation source wire tip. In PCT publication WO 96/14898, Bradshaw et al. propose use of centering balloons which allow blood perfusion around the balloon during treatment. U.S. Pat. No. 5,540,659 to Tierstein suggests use of a helical centering balloon, attached to a catheter at points about the radiation source to allow perfusion through the balloon, between the balloon and radiation ribbon source.

Use of continuous centering balloons, having a beta radiation source within, significantly attenuate the beta radiation when filled with inflation fluid and they may also allow the radiation source to "warp" when placed across curved vessel regions, allowing the balloon to bend but having the central radiation source lying in a straight line between the two ends. Segmented centering balloons may improve the warping problem but may have significant beta attenuation due to blood standing or flowing between the beta source and vessel walls. What remains to be provided is an improved apparatus and method for delivering uniform radiation to vessel interiors to inhibit restenosis. What remains to be provided is an improved perfusion catheter having radiation delivery and drug infusion capabilities.

SUMMARY OF THE INVENTION

The present invention includes devices and methods for providing radiation to the interior of human body vessels. Preferred devices include both devices having spaced apart, sparse helical windings and devices having tightly wound, closely spaced helical or spiral windings. Preferred sparsely wound devices include a helical perfusion balloon, having at least one helical strand configured into multiple windings having the windings spaced apart longitudinally. The preferred device includes a balloon assembly disposed at the distal region of a catheter shaft, where the catheter shaft includes an inflation lumen, a radiation wire lumen, and a drug infusion lumen. In the distal region, the radiation wire lumen can be disposed above the shaft, making room for a distal, single-operator-exchange guide wire lumen. The spiral, inflatable windings are laced inside shaft throughholes transverse to the shaft longitudinal axis and preferably off center. Lacing the helical strand through the shaft secures the helical balloon to the shaft. Lacing the strands also provides positions along the shaft in between windings for the placement of drug infusion apertures. Preferred devices include a tubular sheath over the helical balloon and shaft distal region, defining a perfusion lumen outer wall. The sheath preferably is snugly attached to both the exterior contours of the individual helical balloon strand windings and the catheter shaft.

One sparsely wound device includes a closed end radiation tube extending through a substantial portion of the balloon. This device allows for use and re-use of non-sterilized radiation sources with the sterile catheter. Another device includes an open ended radiation tube terminating distally near the proximal end of the balloon and not extending substantially through the balloon. This device allows extension of a radiation wire or source through the balloon, without having a radiation wire tube within the perfusion lumen within the balloon. The open ended radiation wire tube embodiment provides greater perfusion cross-sectional area due to the lack of the additional tube within the perfusion flow area. The open ended embodiment can also provide a smaller, uninflated profile.

In devices supporting drug infusion, drug infusion apertures extend through the catheter shaft distal region between balloon strand windings. The infused drug exits the apertures into the inter-strand spaces outside the tubular sheath and contacts the inside of the enclosing blood vessel wall. The drug can spread around the outside of the perfusion sheath through the spiral shaped spaces created by the helical strand windings underneath the tubular sheath material. The confined space allows concentrated drug delivery against the vessel wall. It is believed the combined radiation and drug delivery can significantly inhibit restenosis.

Preferred tightly wound or closely spaced helix devices include a helical, perfusion balloon, having at least one helical strand configured into multiple windings. The helical balloon adjacent windings are closely spaced or in contact when inflated so as to have insubstantial space separating them. The tight spiral windings or closely spaced windings improve centering of the catheter in the curved or tortuous vascular system due to many more balloon segments than lobed designs. The balloon is capable of being inflated with a gas. Using gas to inflate the balloon results in decreased absorption of radiation by the inflated balloon interior. The passage of beta radiation is especially improved by use of a gas rather than a liquid for inflation. Gas allows beta radiation to pass relatively unhindered from beta source to the balloon wall.

In a first closely spaced helix embodiment, the catheter device is a "single operator exchange" catheter suitable for use with a removable, preferably sheathed, radiation source. A second closely spaced helix embodiment includes an "over the wire" catheter suitable for use with a removable, preferably sheathed, elongate radiation source. Yet another closely spaced helix embodiment is a single operator exchange device having a combination use lumen partitioned into sterile and non-sterile portions by a permanent sheath extending within the catheter lumen. A guide wire can be inserted through the sterile portion, and a radiation source can be inserted through the non-sterile portion. Maintaining a non-sterile portion separate from contact with the patient allows for use of non-sterilized or non-sterilizable radiation sources, while abating the risk of infection for the patient. Radiation sources in the sterilized portion can be re-used without sterilization, saving considerable time and expense.

Single operator exchange devices according to the present invention can have a proximal, extended entry lumen. This allows for retracting a guide wire distal portion out of the lumen area used in common by both the guide wire and the radiation source. The extended entry lumen is sufficiently long to allow the guide wire to maintain position within the catheter, when lying within, yet does not interfere with insertion of the radiation source through the length of the catheter.

In use, the above mentioned devices can be used for irradiation only, drug infusion, or for concurrent irradiation, drug infusion, and angioplasty. The devices can be advanced over a guide wire, the guide wire retracted, the balloon inflated and the radiation source inserted. After angioplasty and/or irradiation and/or drug infusion are complete, the radiation source can be retracted, the guide wire advanced, and the catheter retracted over the guide wire while maintaining the wire across the treated area.

The present invention also provides a radiation delivery system that permits the use of an open-ended delivery lumen without the risk of blood contamination and without the need to dispose of or resterilize the radiation source. In addition, the present invention provides a radiation delivery system that permits beta radiation to be delivered through a balloon without a significant decrease in radiation exposure to the treatment site, even in large vessels.

One embodiment of the present invention may be described as a catheter having an open-ended lumen, a radiation source disposed in the open-ended lumen of the catheter and a closed-end sheath surrounding the radiation source. The closed-end sheath prevents blood or other fluids from coming into contact with the radiation source so that blood does not contaminate the radiation source and it may be reused. The catheter may be a balloon catheter and may include a guide wire disposed in the open-ended lumen of the catheter. The open-ended lumen may be a full-length lumen or a partial-length lumen (e.g., a rapid exchange lumen). Preferably, the lumen is centered in the balloon for uniform radiation delivery. The catheter may also include a blood perfusion lumen under the balloon or around the balloon. The open-ended lumen in the catheter may have a reduced diameter adjacent the distal end of the catheter to prevent the radiation source from exiting the lumen. Alternatively, the closed-end sheath may have a ridge which abuts a corresponding restriction in the open-end lumen of the catheter to prevent the radiation source from exiting the lumen.

Another embodiment of the present invention may be described as a method of delivering radiation to a treatment site inside the vasculature of a patient using the radiation delivery system described above wherein the method includes the steps of (1) inserting the catheter into the vasculature of a patient; (2) inserting the radiation source into the closed-end sheath; (3) inserting the radiation source and the closed-end sheath into the lumen of the catheter such that the radioactive portion is positioned adjacent a treatment site; and (4) exposing the vascular wall to radiation from the radiation source. Alternatively, the sheath may be inserted into the catheter before the radiation source is loaded into the sheath. The method may also include the steps of (5) removing the radiation source from the catheter; and (6) removing the catheter from the patient. The catheter may be inserted into the vasculature over a guide wire and the guide wire may be removed from the catheter prior to exposing the vascular wall to radiation.

Yet another embodiment of the present invention may be described as a method of delivering radiation to a treatment site inside the vasculature of a patient using a gas-filled balloon catheter and a radiation source wherein the method includes the steps of: (1) inserting the catheter into the vasculature such that the balloon is adjacent to a treatment site; (2) inflating the balloon with a liquid or gas; (3) inserting the radiation source into the catheter such that the radioactive portion is adjacent to the balloon; and (4) exposing the treatment site to radiation from the radiation source through the gas in the balloon. The balloon may be inflated prior to or subsequent to inserting the radiation source. Preferably beta radiation is used, but other radioisotopes may be employed.

BRIEF DESCRIPTION OF THE DRAWINGS

FIG. 3 is a side view of an alternative embodiment of the present invention including a helical-shaped balloon;

FIG. 4 is a side view of an alternative embodiment of the present invention including a toroidal-serpentine-shaped balloon;

FIGS. 5a, 5b and 5c are partially sectioned side views of an alternative embodiment of the present invention including a rapid-exchange guide wire lumen;

FIG. 6 is a partially sectioned side view of an alternative embodiment of the present invention including a perfusion lumen passing through the balloon;

FIG. 7 is a cross-sectional view taken at B—B in FIG. 6;

FIG. 11 is a lengthwise, longitudinal cross-sectional view of an over-the-wire catheter according to the present invention;

FIG. 12 is a lengthwise, longitudinal cross-sectional view of a single operator exchange catheter having a sheath according to the present invention;

FIG. 13 is a lengthwise, longitudinal cross-sectional view of the catheter of FIG. 12 having a guide wire inserted past the sheath;

FIG. 14 is a cross-sectional view of the catheter of FIG. 13 taken through 14—14;

DETAILED DESCRIPTION OF THE PREFERRED EMBODIMENTS

Figure 1:
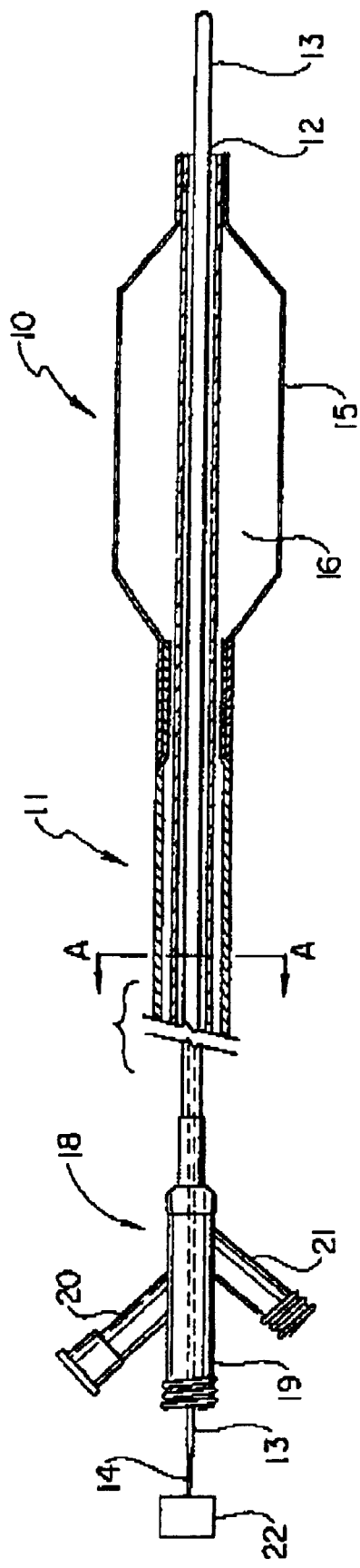
FIG. 1 is a partially sectioned side view of an embodiment of the present invention.
Figure 2:
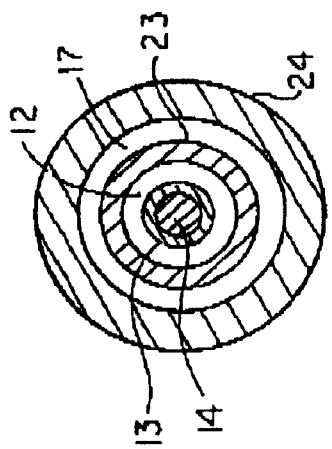
FIG. 2 is a cross-sectional view taken at A—A in FIG. 1.

Refer now to FIGS. 1 and 2 which illustrate one embodiment of a radiation delivery system 10 of the present invention. Radiation delivery system 10 includes a catheter 11 having an open-ended lumen 12 extending therethrough. A closed-ended sheath 13 surrounds a radiation source 14 (such as a guide wire) disposed in the open-ended lumen 12. An after-loader 22 may be connected to the proximal end of the radiation source 14 to advance and retract the radiation source 14 and safely contain it when not in use.

The catheter 11 includes an inflatable balloon 15 having an interior 16 which is in fluid communication with an inflation lumen 17. The catheter 11 illustrated in FIGS. 1 and 2 has a coaxial shaft construction including an inner tube 23 and an outer tube 24. Other shaft constructions may be employed such as a dual lumen shaft design illustrated in FIG. 6. A manifold 18 is connected to the proximal end of the catheter 11 and includes a guide wire port 19 and a flush port 20 both of which are in fluid communication with the open-ended lumen 12. The guide wire port may include a toughy-borst (not shown) to seal about the proximal end of the closed-end sheath 13. The manifold 18 also includes an inflation port 21 which is in fluid communication with the inflation lumen 17 and the interior 16 of the balloon 15.

The closed-end sheath 13 preferably extends to the proximal end of the catheter 11 and may include means for connection to the after-loader 22. The closed-end sheath 13 may be formed of polyethylene, PTFE coated polyimide or other suitable flexible material. The closed-end sheath 13 may have a length of about 100 to 300 cm depending on the length of the catheter 11. A wall thickness between 0.0002 and 0.005 inches is preferred to minimize profile and radiation absorption.

As included with catheter 11 illustrated in FIGS. 1 and 2, the open-ended lumen 12, closed-ended sheath 13, radiation source 14, after loader 22 and toughy-borst are also included with catheters 31, 41, 51 and 61 as illustrated in FIGS. 3, 4, 5 and 6, respectively. In addition, those skilled in the art will appreciate that the various features of each catheter 11, 31, 41, 51 and 61 may be mixed and matched depending on the desired result. For example, the rapid exchange features of catheter 51 may be incorporated into perfusion catheter 61, resulting in a perfusion rapid exchange catheter for the delivery of radiation. As another example, the centering balloon 35 or 45 may be contained inside balloon 15 of catheters 11 and 61 to provide a centering function, even in curved vasculature.

Refer now to FIGS. 3 and 4 which illustrate alternative radiation delivery catheters 31 and 41. Alternative catheters 31 and 41 may be used in place of catheter 11 for the radiation delivery system 10 illustrated in FIG. 1. Except as described herein, the design and use of alternative catheters 31 and 41 is the same as catheter 11. Alternative catheter 41 may be made as described in co-pending U.S. patent application Ser. No. 08/608,655 which is incorporated herein by reference. Similarly, alternative catheter 31 may be made as described in the above-referenced case except that the balloon 35 is wound in a helical shape rather than a serpentine shape.

With reference to FIG. 3, alternative catheter 31 includes a helically-shaped balloon 35 which is wound around the distal end of the catheter 31. When the helically-shaped balloon 35 is inflated, a helically-shaped perfusion path 36 is defined between the balloon 35, the shaft 37 and the inside surface of the blood vessel. The blood perfusion path 36 allows blood to flow across the treatment site while the balloon 35 is inflated. In addition, the concentric and flexible helical shape of the inflated balloon 35 maintains the distal portion of the catheter 31 centered in the vessel, even around turns in the vasculature. Having the catheter 31 centered in a vessel permits the uniform distribution of radiation to the treatment site.

The distal end of the shaft 37 may include a reduced diameter tip 38 with a corresponding reduced inside diameter open-ended lumen (not visible). The reduced inside diameter permits a conventional guide wire to exit out the distal end of the catheter 31 but prohibits the sheath 13 and radioactive source wire 14 from exiting. This assumes, of course, that the sheath 13 or radioactive source wire 14 is larger than the guide wire. A reduced diameter tip may be included on any of the catheters described herein.

With reference to FIG. 4, alternative catheter 41 includes a toroidal-serpentine-shaped balloon 45. When the serpentine-shaped balloon 45 is inflated, a linear perfusion path 44 is defined between the balloon 45, the shaft 47 and the inside surface of the blood vessel. The blood perfusion path 44 allows blood to flow across the treatment site while the balloon 45 is inflated. As with the helical balloon described above, the concentric and flexible serpentine shape of the inflated balloon 45 maintains the distal portion of the catheter 41 centered in the vessel, even around turns in the vasculature. Having the catheter 41 centered in a vessel permits the uniform distribution of radiation to the treatment site. A further advantage of the serpentine-shaped balloon 45 is the relative linearity of the perfusion path 44 which tends to minimize resistance to blood flow.

Catheter 41 may also include two radiopaque markers 46 to facilitate radiographic placement in the vasculature. The distal end of the shaft 47 may include a reduced diameter tip 48 with a corresponding reduced inside diameter open-ended lumen (not visible). The reduced inside diameter permits a conventional guide wire to exit out the distal end of the catheter 41 but prohibits the sheath 13 and radioactive source wire 14 from exiting.

It is also contemplated that both the helical balloon 35 and the serpentine balloon 45 may be covered with an elastomeric sleeve to aid in collapsing the balloon 35/45 upon deflation. This sleeve would be connected to the shaft adjacent the proximal and distal ends of the balloon 35/45. It is further contemplated that this sleeve may include perfusion holes both proximally and distally to permit blood perfusion along the perfusion path 36/44 defined by the balloon 35/45. If a gas is used to inflate the balloon 35/45 in large diameter vessels (e.g., peripheral vasculature), it is preferred to not permit perfusion of blood which would otherwise absorb beta radiation. In such a situation, the sleeve would not include perfusion holes.

Figure 5A:
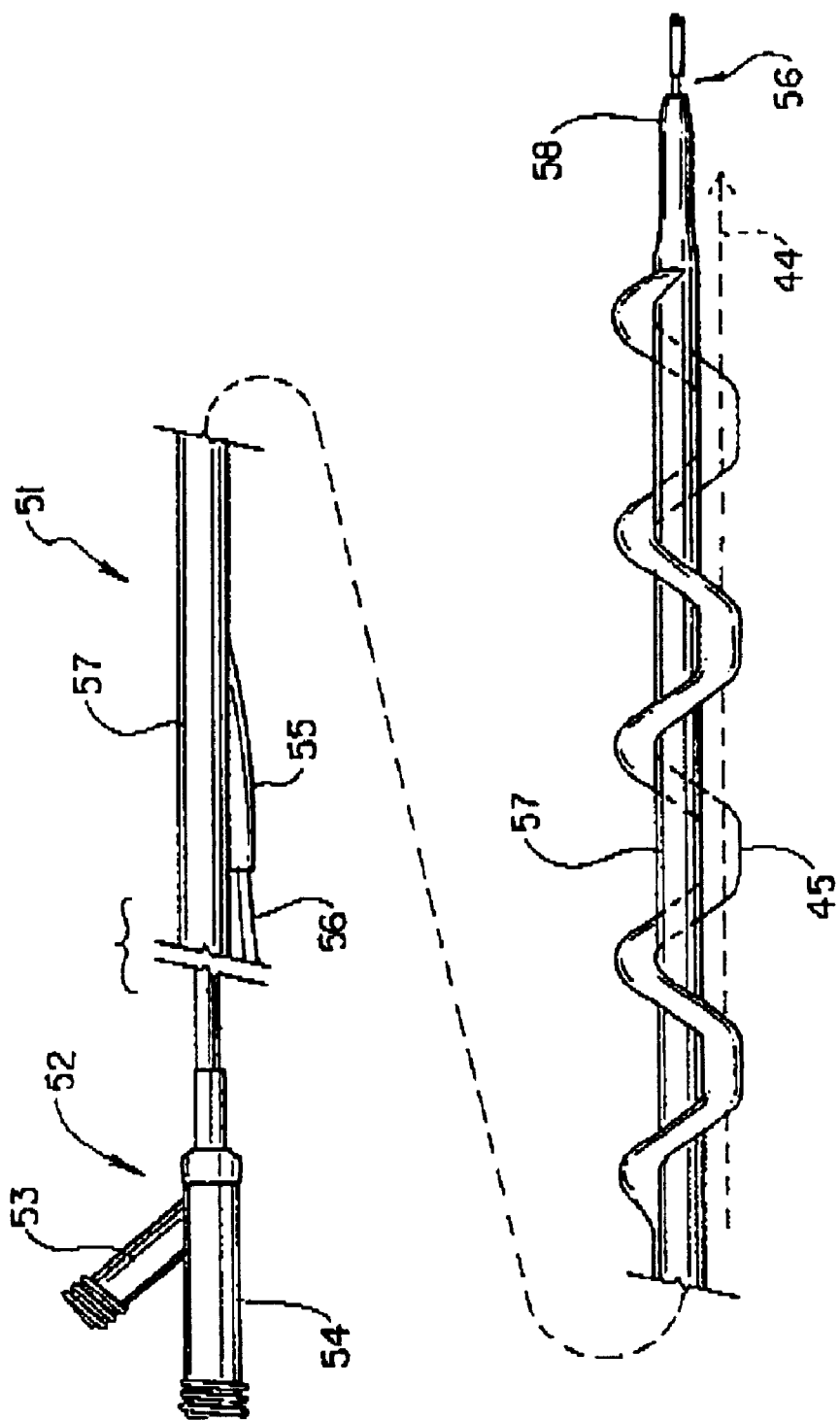
Figure 5B:
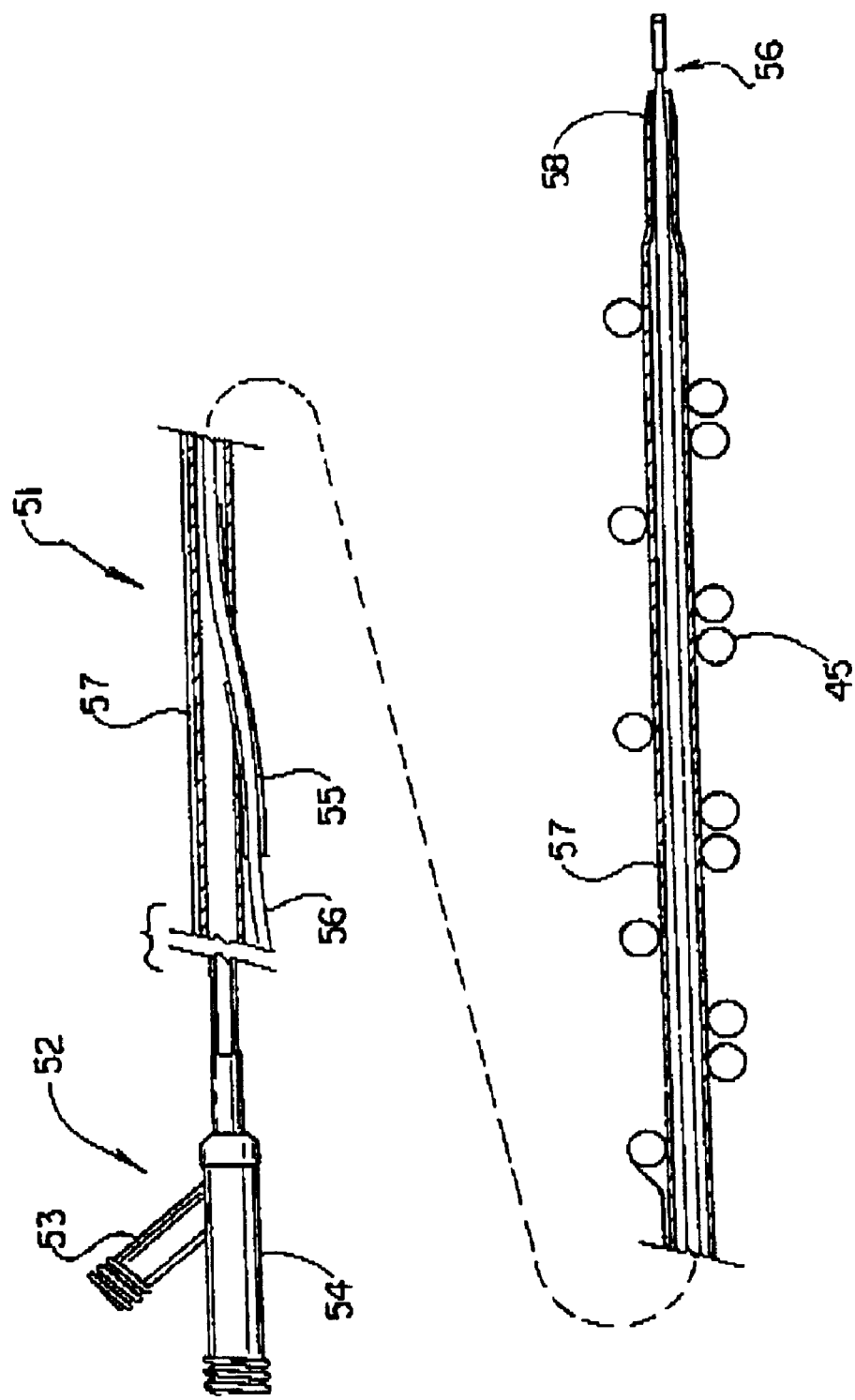

Refer now to FIGS. 5a, 5b and 5c which illustrate a rapid-exchange embodiment of the present invention. Alternative catheter 51 may be used in place of catheter 11 for the radiation delivery system 10 illustrated in FIG. 1. Except as described herein, the design and use of alternative catheter 51 is the same as catheter 11.

Rapid-exchange catheter 51 includes an elongate shaft 57 with a manifold 52 connected to the proximal end and a balloon 45 connected to the distal end. Although catheter 51 is shown with a serpentine balloon 45 and a corresponding linear perfusion path 44, any of the balloon types described herein may be used.

The manifold 52 includes a balloon inflation port 53 which is in fluid communication with the balloon 45 via a conventional inflation lumen. A radiation source entry port 54 is also included in the manifold 52. The entry port 54 communicates with the open-ended lumen and permits the insertion of the sheath 13 and radiation source 14. The open-ended lumen terminates in a reduced diameter tip 58 which permits a conventional guide wire 56 to exit out the distal end of the catheter 51 but prohibits the sheath 13 and radioactive source wire 14 from exiting.

The guide wire 56 enters the shaft 57 at the proximal guide wire tube 55. The guide wire tube 55 is located near the distal end of the catheter to permit catheter exchange without the need for an extension wire or wire trapping device. As best seen in FIG. 5c, the guide wire tube 55 has sufficient length such that the guide wire 56 may be pulled back and out of the open-ended lumen. In particular, the distance from the proximal end of the guide wire tube 55 to the distal end of the catheter 51 is less than the length of the guide wire extending outside of the patient's body. With the guide wire pulled back, the radioactive source wire 14 and the sheath 13 may be inserted into the entry port 54 to the distal end of the catheter 51.

Refer now to FIGS. 6 and 7 which illustrate an alternative perfusion catheter 61. Alternative catheter 61 may be used in place of catheter 11 for the radiation delivery system 10 illustrated in FIG. 1. Except as described herein, the design and use of alternative catheter 61 is the same as catheter 11.

Perfusion catheter 61 includes an elongate shaft 67 with a manifold 18 connected to the proximal end and a balloon 16 connected to the distal end. The shaft 67 is a multi-lumen type extrusion including an open-ended lumen 62 and an inflation lumen 63. Inflation lumen 63 provides fluid communication between the inflation port 21 and the interior of the balloon 16. Open ended lumen 62 is in communication with entry port 19 for the insertion of a guide wire (not shown) or the radioactive source 14 and sheath 13. A guide wire extension tube 64 is connected to the distal end of the multi-lumen shaft 67 and rigidly connects to the distal end of the balloon 15.

Catheter 61 includes a series of perfusion ports 65 which are in fluid communication with the distal portion of the open-ended lumen 62. The perfusion ports 65 permit blood to flow across the treatment site via the open-ended lumen while the balloon 15 is inflated.

Figure 8:
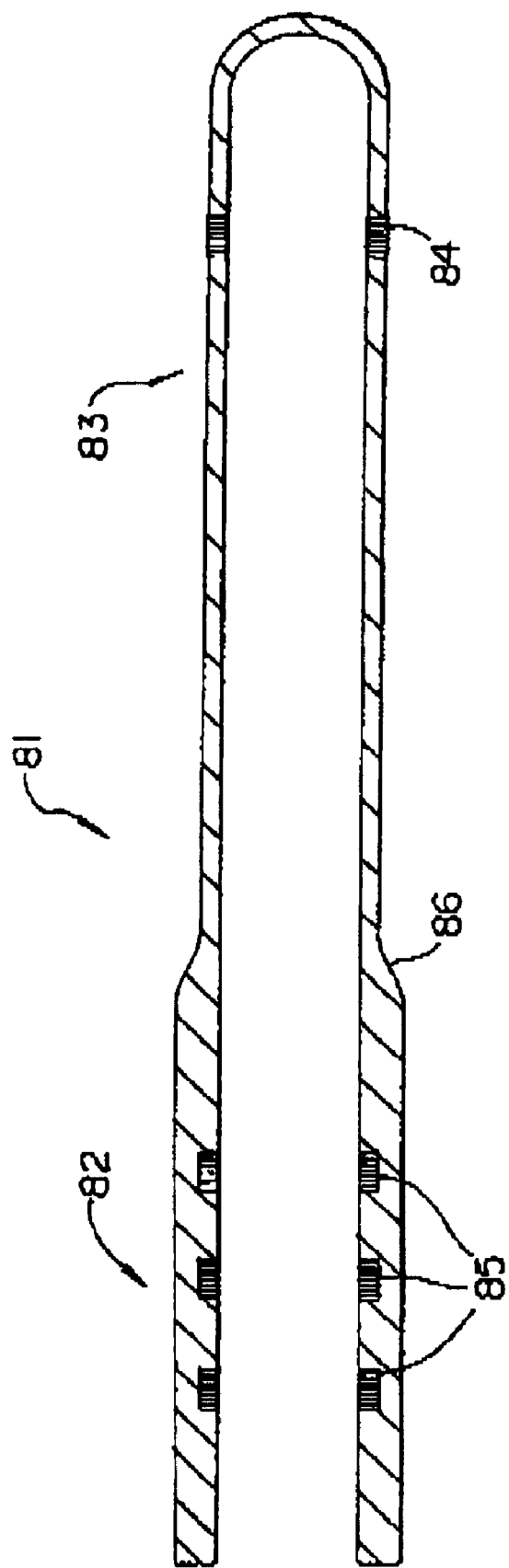
FIG. 8 is a cross-sectioned side view of an alternative sheath of the present invention.

With reference now to FIG. 8, an alternative sheath 81 is illustrated. Alternative sheath 81 may be used in place of sheath 13 for the radiation delivery system 10 illustrated in FIG. 1. Except as described herein, the design and use of alternative sheath 81 is the same as sheath 13.

Sheath 81 includes a proximal portion 82 and a distal portion 83, wherein the proximal portion 82 includes a relatively thicker wall and larger outside diameter. The thicker wall tends to absorb radiation to reduce the amount of unwanted exposure, particularly exposure of the medical personnel. The larger outside diameter of the proximal portion 84 may be used in conjunction with a corresponding restriction in the open-ended lumen 12 of any of the catheters described herein. Specifically, the leading edge or ridge 86 of the proximal portion 82 may abut a mating restriction in the open-ended lumen 12 such that the sheath 81 cannot be advanced beyond that point. The leading edge 86 and the mating restriction in the open-ended lumen serve the same function as the reduced diameter tip described previously and may be used in lieu thereof. In other words, the leading edge 86 and the mating restriction in the open-ended lumen would permit a conventional guide wire 56 to exit out the distal end of the catheter but would prohibit the sheath 81 and radioactive source wire 14 from exiting the distal end of the catheter.

The closed-end sheath 81 may include means for connection to the after-loader 22. The closed-end sheath 81 may be formed of polyethylene, PTFE coated polyimide or other suitable flexible material. The closed-end sheath 81 may have a length of about 100 to 300 cm depending on the length of the catheter 11. On the distal portion 83, a wall thickness between 0.0002 and 0.005 inches is preferred to minimize profile and radiation absorption. On the proximal portion 82, a wall thickness between 0.040 and 1.0 inches is preferred to maximize radiation absorption without significantly compromising profile. The outside diameter of the proximal portion 82 may be greater than the vascular access size on the portion of the sheath 81 that remains outside the body. Once the radiation source is inside the body, the risk of exposure of beta radiation to medical personnel is diminished.

Sheath 81 may also include a radiopaque marker 84 to facilitate radiographic placement of the sheath 81 and radioactive wire 14. Such a radiopaque marker 84 may also be included on sheath 13.

Sheath 81 may also include a series of annular magnets 85. Magnets 85 may be used to interact with a series of magnets connected to the catheter 11, 31, 41, 51 or 61 or a series of magnets connected to a guide catheter (not shown). This general arrangement is described in more detail in PCT publication WO 95/21566 which is fully incorporated herein by reference. The interacting magnets provide a means to longitudinally control and stabilize the position of the radiation source relative to the patient and treatment site.

In practice, catheters 11, 31, 41, 51 and 61 may be used to delivery radiation to the vascular wall in the following manner. After vascular access is established and a guide catheter is in position (if desired), the catheter 11/31/41/51/61 is inserted into the patient with the distal portion adjacent the treatment site. If a guide wire is used, the guide wire may be inserted prior to or simultaneously with the catheter. The balloon is then inflated to a low pressure sufficient to center the balloon in the vasculature and prevent movement of the catheter relative to the treatment site. Optionally, the balloon may first be inflated to a higher pressure in order to dilate the treatment site. If desired, the balloon may be inflated with a gas such as nitrogen, carbon dioxide or other non-toxic gas to minimize the absorption of radiation by the inflation media. After dilatation, the balloon is maintained in an inflated state, preferably at a low pressure, to center the catheter in the vascular lumen. The sheath 13 is placed over the radiation wire 14, preferably ahead of time, and the two are advanced into the open-ended lumen using an after-loader system. Optionally, the sheath 13 is first loaded into the open-ended lumen of the catheter and the proximal end of the sheath is connected to the after-loader, followed by insertion of the radioactive source wire 14. The toughy-borst is maintained sufficiently loose to allow advancement and may be locked to fully seal about the sheath 13 once the radiation wire 14 and sheath 13 are in the desired position. If a guide wire is used in the open-ended lumen, the guide wire is preferably retracted to permit passage of the radioactive wire 14 and sheath 13. If a rapid exchange catheter 51 is used, the guide wire is pulled back into the proximal guide wire tube 55. The vascular wall is then exposed to radiation (preferably beta radiation) for the desired period of time. The radioactive wire 14 and sheath 13 are removed from the catheter 11/31/41/51/61 and the catheter is removed from the patient.

Figure 9:
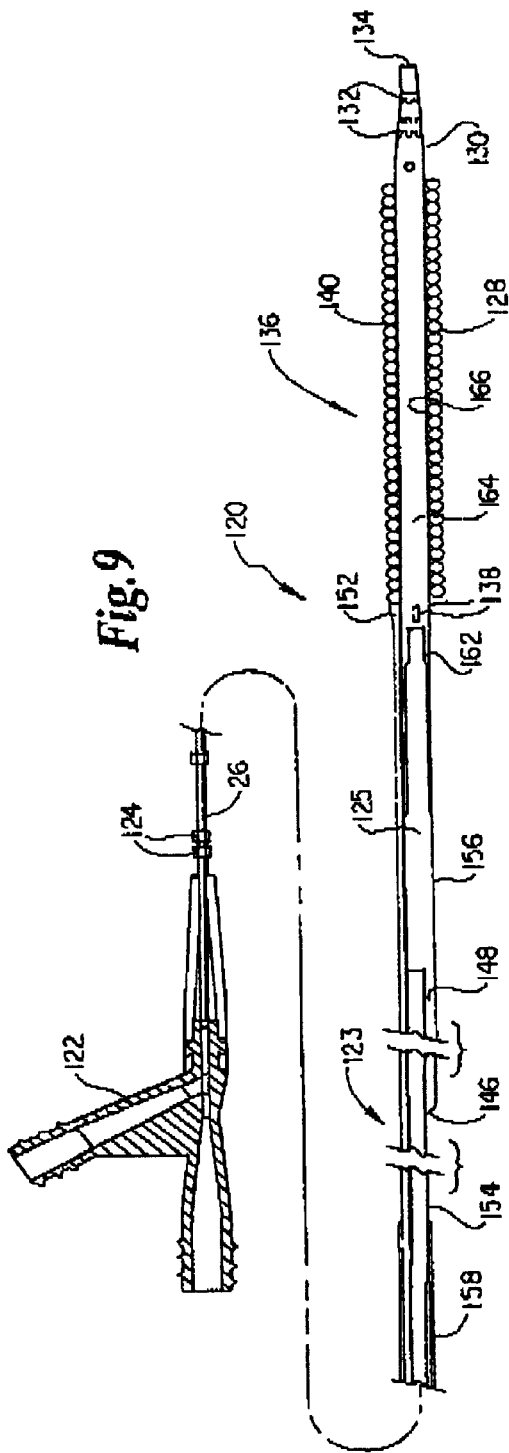
FIG. 9 is a lengthwise, longitudinal cross-sectional view of an single operator exchange catheter according to the present invention.

FIG. 9 illustrates a catheter 120 suitable for single operator exchange according to the present invention. Catheter 120 is illustrated attached to a manifold 122, extending from a proximal portion 126, to a distal portion 128, to a distal end 130. An elongate catheter shaft 123 includes a proximal outer tube 158, an inner tube 154, an intermediate outer tube 156, and a necked inner tube 162. A perfusion head 136 is located near catheter distal portion 128. Perfusion head 136 includes a balloon 140 disposed about a perfusion tube 166 which defines a perfusion lumen 164. Perfusion lumen 164 can transport blood from proximal perfusion ports 138 through to distal perfusion ports 132. A proximal guide wire port 146 and extended entry guide wire lumen 148 allow insertion of a guide wire (not shown) through the catheter and out distal port 134.

Figure 10:
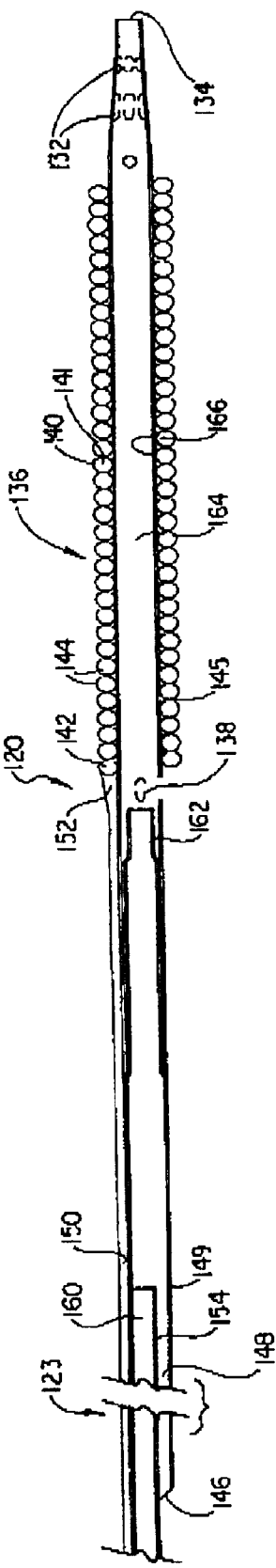
FIG. 10 is an enlarged, lengthwise longitudinal cross-sectional view of a distal portion of the catheter of FIG. 9.

Referring now to FIG. 10, an enlarged view of a proximal portion of catheter 120 is illustrated. Balloon 140 as illustrated, includes a single strand 142 formed into a series of helical windings 144 about perfusion lumen 164. Windings 144 are closely adjacent (preferably in contact when inflated) to each other, having little or no inter-strand spacing, as indicated at 145. An inflation lumen 150, extending proximally from balloon 140, is in fluid communication with the interior of balloon 140, indicated at 141. Helical balloon 140 serves to center perfusion lumen 164, and anything contained within, useful when the balloon is inflated in vessel curves or bends.

In use, a guide wire can be inserted within the vasculature of a patient and advanced to a stenosed site to be treated.

Catheter 120 can then have the guide wire proximal end inserted through distal port 134, through the balloon portion, through extended entry lumen 148, and proximally out proximal guide wire port 146. With the guide wire thus threaded, catheter perfusion head 136 can be advanced to the site to be treated. Once in position, a gas under pressure can be used to inflate balloon 140. Either before, during, or after balloon inflation, the guide wire can be partially retracted such that the guide wire distal end is generally near the distal end of extended entry lumen 148, indicated at 149. The length of extended entry lumen 148 is such that the guide wire is able to maintain its position within the extended entry lumen without falling out. The guide wire should not extend distally so far that it interferes with advancement of a radioactive source, discussed below.

With the guide wire thus in position, a radioactive source can be advanced from catheter proximal portion 126 through shaft 123 past the distal end of inner tube 154, indicated at 149. A preferred radiation source is a beta emitter, but other radiation sources are contemplated and are within the scope of the invention. One preferred source is Nickel-66. The radioactive source can be advanced further, within perfusion lumen 164 within balloon 140. The radioactive source outside diameter is small enough, and perfusion lumen inside diameter large enough, that sufficient blood is able to perfuse around the radioactive source and through perfusion lumen 164.

With the radiation source thus disposed, the radiation is able to pass relatively unhindered through the gas filled interior 141 of balloon 140 to the surrounding vessel walls. In one method, the pressure is such that concurrent angioplasty and irradiation are carried out. In another method, only irradiation is performed, requiring lower gas pressure. In either of the aforementioned two methods, pressure is supplied sufficient to bring balloon 140 into close contact with the surrounding vessel walls. This excludes substantially all of the blood and external perfusing blood flow from between the balloon exterior and the vessel walls. This removal of interposing blood removes a source of beta radiation attenuation.

Once the radiation exposure period is complete, the radiation source can be withdrawn, and the guide wire can be advanced distally once more. In a preferred method, the radiation source is enclosed in a sheath. This allows for use of a non-sterile radiation source. This allows for use and re-use of a radiation source without requiring either sterilization or disposal of the radiation source. Sterilization or disposal is normally required after use, as the elongate radiation source has been in contact with the patients blood. This contact contaminates the exposed radiation source, requiring either disposal or subsequent sterilization. The sheath can be deployed within the catheter prior to radiation source advancement or slid over the radiation source outside of the catheter, and the sheathed source inserted into the catheter as a unit.

Referring now to FIG. 11, an "over-the-wire" embodiment of the present invention is illustrated. Catheter 121 is similar in many respects to catheter 120 of FIG. 9, but having an outer tube 157 having no proximal guide wire port suitable for "single operator exchange". Rather, catheter 121 is suitable for use over a guide wire, where the guide wire extends from proximal portion 126 through distal portion 128 and out distal port 134.

In use, a guide wire is positioned near a site to be treated. Catheter 121 can then be advanced over the guide wire, positioning perfusion head 136 near the treatment site. Inflation gas can them be supplied via inflation lumen 150, inflating balloon 140 against the vessel walls. The guide wire can be withdrawn proximally out of the catheter, either before or after balloon inflation. A radioactive source, preferably in a sheath, can then be advanced distally through the catheter, advancement stopping when the radioactive source distal region is disposed within balloon 140.

With the radioactive source disposed within the balloon, radiation treatment can continue for the appropriate time. The advantages of using a sheath, a gas filled balloon, and a tight, helical balloon are described above with respect to the embodiment of FIG. 9. Once treatment is complete, the radiation source can be withdrawn.

Referring now to FIG. 12, a "single operator exchange" catheter 220 having a fixed sheath is illustrated. Catheter 220 is similar in many respects to catheter 120 of FIG. 9, with some similar reference numerals omitted for clarity. Catheter 220 includes a sheath 250 within shaft 123, sheath 250 having a proximal portion 252 and a distal portion 254, and is preferably fixed within shaft 123, using a method such as adhesive bonding. A guide wire 222 is illustrated inserted into guide wire proximal entry port 146, lying within extended entry lumen 148. Guide wire 222 has a distal end 226, indicating inserted as far as 224 in FIG. 12.

FIG. 13 illustrates catheter 220 of FIG. 12 having guide wire 222 inserted distally past distal port 134, to necked inner 162. In this configuration, catheter 220 can be advanced or retracted over guide wire 222. Sheath 250 is partially displaced radially by the insertion of the guide wire and does not interfere with guide wire insertion. FIG. 14 illustrates a cross section of catheter 220 taken through 14—14 in FIG. 13, showing that flexible sheath 250 is partially displaced by guide wire 222 being inserted through catheter 220. Both sheath 250 and guide wire 222 are shown within necked inner tube 162. The displacement of sheath 250 is indicated also at 255 in FIG. 13. With guide wire 222 this far inserted, in preferred embodiments, there is insufficient room for insertion of an elongate radioactive source through to perfusion head 136.

Catheter 220 is used in a similar manner to catheter 120 of FIG. 9. Sheath 250 however is displaced by guide wire 222 during catheter advancement and retraction, when the radiation source is withdrawn sufficiently proximally so as to not interfere with guide wire movement within the catheter. Sheath 250 is at least partially filled by an elongate radiation source during radiation exposure of the vessel site. When sheath 250 is containing a radiation source, guide wire 222 is withdrawn sufficiently proximally so as to not interfere with radiation source placement yet lying sufficiently within the extended entry lumen 146 so as maintain guide wire position within the catheter.

Sheath 252 is an illustration of one aspect of the invention, the partitioning of a lumen into sterile and non-sterile portions. In FIG. 12, sheath lumen 252 does not have to be sterile, since it is not in contact with blood. Shaft lumen 125 external to sheath 252 is sterile to prevent patient exposure to infection. This partitioning, accomplished with a flexible partitioning means, allows dual, though not necessarily simultaneous, uses of a lumen. The distal portion of the lumen can be occupied by a disposable guide wire in the sterile portion during catheter advancement or retraction. The distal portion of the lumen can be occupied by a reusable, not necessarily sterile or sterilizable, radiation source once the catheter is in place. The catheter perfusion head 36 profile can thus be kept small by allowing sufficient lumen space for only the guide wire or the radiation source at one time, not both.

Totally enclosing the radiation source in a sheath illustrates one embodiment of the invention. In another embodiment, the lumen is partitioned into sterile and non-sterile portions by dividing the lumen along a longitudinal axis with a flexible wall or membrane, the wall extending across an intermediate portion of the lumen. In this later embodiment, the sterile portion of the lumen is formed in part by a flexible wall and in part by the usually more rigid lumen walls. Furthermore, in one embodiment, this flexible wall need extend longitudinally only from near the guide wire proximal entry port to near the lumen distal end. The remaining proximal portion of the lumen need not be divided by the wall in a single operator exchange embodiment, where there is no need to insert a guide wire.

Figure 15:
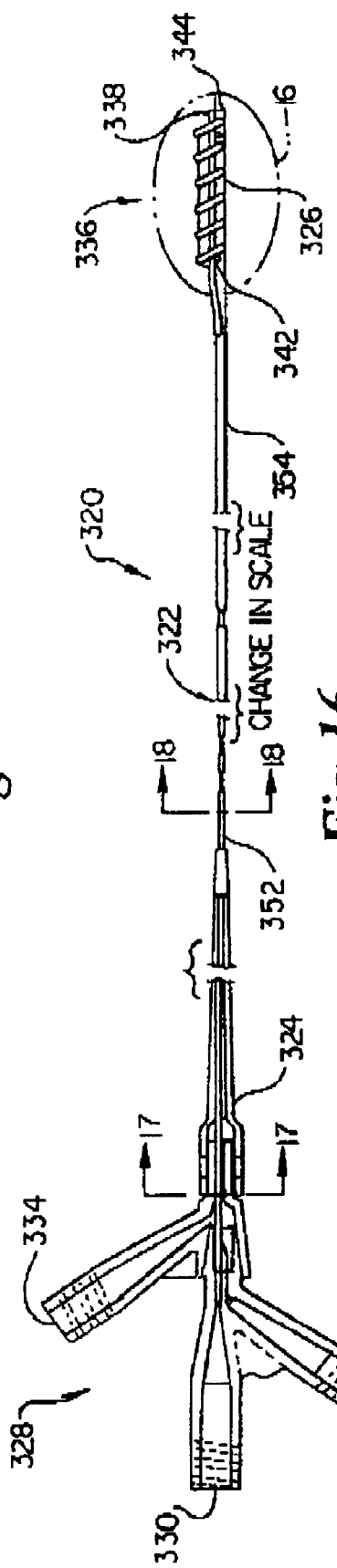
FIG. 15 is a fragmentary, side view of a sparsely wound balloon on a radiation delivery catheter.

FIG. 15 illustrates a sparsely wound radiation delivery catheter 320 including a tubular shaft 322 having a proximal region 324 and a distal region 326, a manifold 328 disposed near shaft proximal region 324, a balloon assembly 336 disposed on shaft distal region 326, and a distal tip 338. Shaft 322 includes a proximal shaft portion 352 and a distal shaft portion 354 and is preferably formed of polyethylene. Manifold 328 includes a radiation wire port 330, an inflation port 332, and an infusion port 334. Radiation port 330 is used to insert an elongate radiation emitting member. Inflation port 332 is used to admit an inflation fluid to balloon assembly 336. Infusion port 334 can be used to infuse drugs through to balloon assembly 336. The present invention can be made in accordance with the drug delivery catheters described in U.S. Pat. No. 5,558,642, herein incorporated by reference.

In one embodiment, a catheter according to the present invention includes inflation and radiation wire lumens, but no infusion lumen. FIG. 15 illustrates a preferred embodiment catheter 320 having an infusion lumen as well. The inflation, radiation, and infusion lumens in preferred embodiments extend through shaft 322 to balloon assembly 336. A preferred embodiment includes a distal, single-operator-exchange guide wire lumen having a proximal port 342 and a distal port 344.

Figure 16:
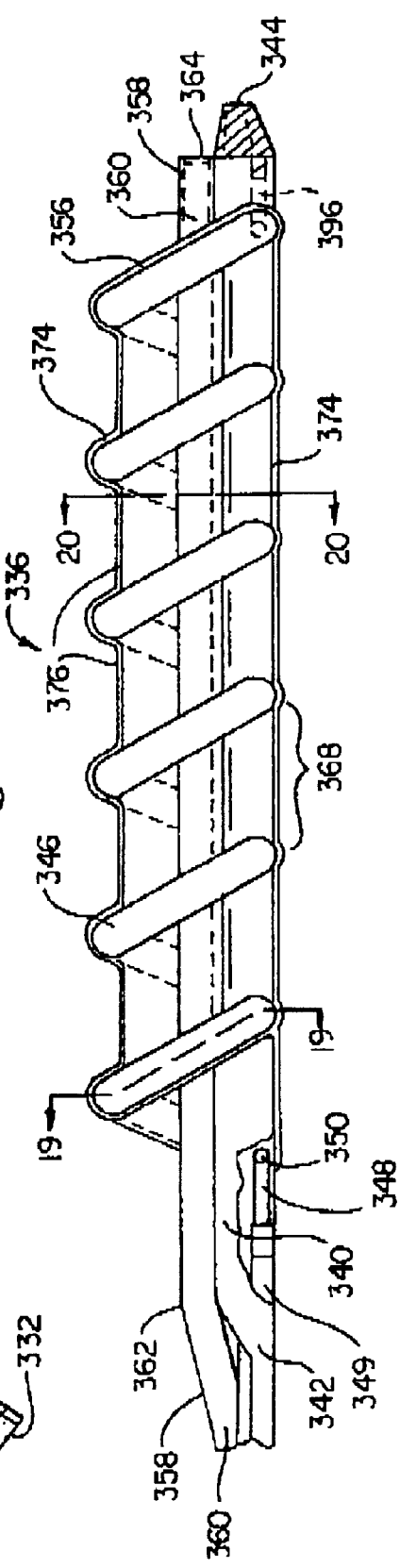
FIG. 16 is a fragmentary, side view of the distal region of the catheter of FIG. 15.
Figure 17:
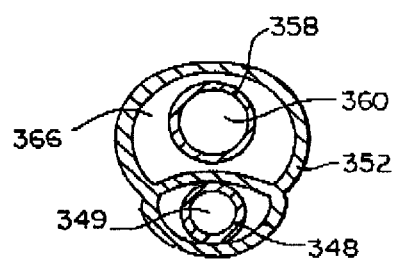
FIG. 17 is a cross-sectional view taken through line 17—17 in FIG. 15, illustrating a proximal catheter shaft cross-section.
Figure 18:
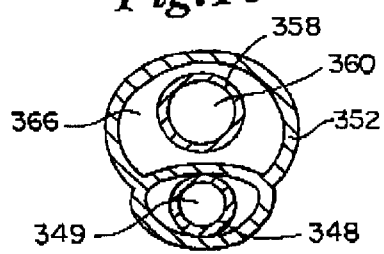
FIG. 18 is a cross-sectional view taken through line 18—18 in FIG. 16, illustrating a distal catheter shaft cross-section.
Figure 19:
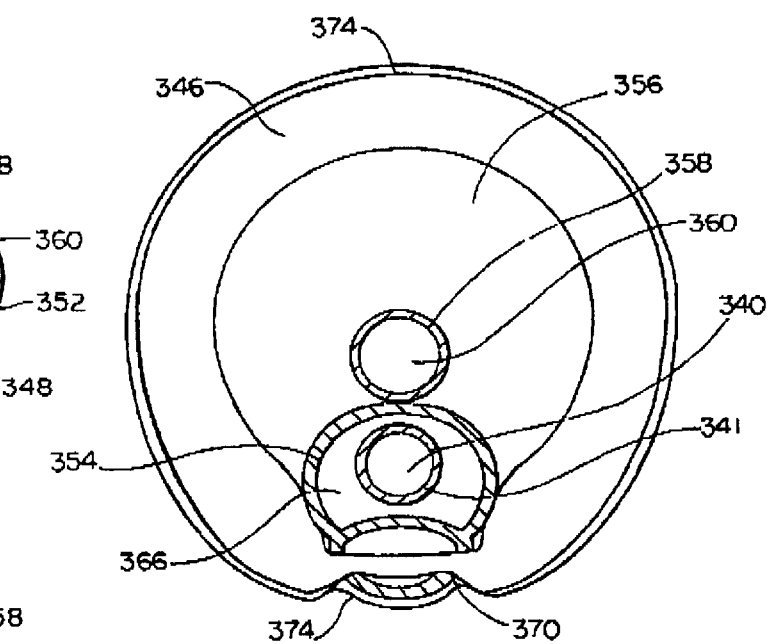
FIG. 19 is a cross-sectional view taken through line 19—19 in FIG. 16, projected through one complete inflation coil revolution.
Figure 20:
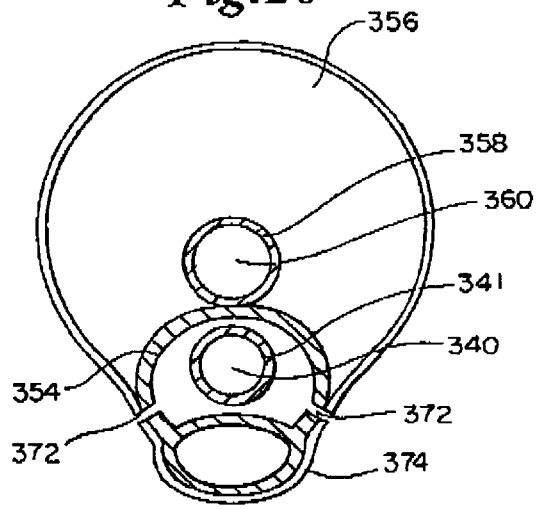
FIG. 20 is a cross-sectional view taken through line 20—20 in FIG. 16, shown without the inflation coil, illustrating infusion openings.

Referring now to FIGS. 16, 19 and 20, FIG. 16 illustrates detail area 16 of FIG. 15, showing balloon assembly 336 in more detail in an inflated state. A radiation wire tube 358 defines a radiation wire lumen 360, rising near radiation tube region 362 near proximal guide wire port 342 to accommodate entering guide wire tube 341 below, extending through a substantial portion of balloon assembly 336, and ending in a radiation wire tube distal closed end 364. Closed end 364 prevents fluid communication between bodily fluids and radiation wire lumen 360, allowing use and re-use of radiation sources within the closed lumen without sterilization. The closed lumen allows use of non-sterile sources within a sterile catheter, as the radiation source does not contact the blood stream and become contaminated. In a preferred embodiment, the radiation wire tube lies external to the catheter shaft within the balloon assembly, as illustrated by radiation wire tube distal portion 358 lying atop shaft distal portion 354 in FIGS. 16, 19 and 20. Radiation wire tube 358 can be formed of polyimide or PTFE. In a preferred embodiment, radiation wire tube 358 includes a distal segment formed of a collapsible polyolefin copolymer (POC) material within balloon assembly 336, enabling increased perfusion when not occupied by a radiation wire.

Guide wire tube 341 extends from proximal entry port 342 through distal guide wire port 344. Guide wire tube 341 is preferably formed of polyethylene. In a preferred embodiment, guide wire lumen 340 lies within shaft distal portion 354. In catheter 320, an infusion lumen 366 is defined between the outside walls of guide wire tube 341 and the inside walls of shafts 354 and 352, as illustrated by FIGS. 17, 18, 19 and 20.

In the embodiment shown, a helical balloon is formed of at least one inflatable helical strand or coil 346 having multiple windings extends longitudinally over a substantial portion of balloon assembly 336. Balloon strand 346 is preferably formed of polyolefin. Balloon strand 346 is in fluid communication with an inflation lumen 349 within an inflation tube 348 and preferably has a blind, distal termination 396. Inflation lumen 349 preferably lies within shafts 352 and 354, as illustrated by inflation tube 348 lying within shafts 352 and 354. Inflation tube 348 is preferably formed of polyimide. Balloon strand 346 can be attached to inflation tube 348 as illustrated at 350. Balloon inflatable strand 346, in an inflated state, defines a perfusion lumen 356 therethrough, as indicated in FIGS. 16, 19 and 20. Perfusion lumen 356 does not lie uniformly around shaft 354 in a preferred embodiment, but has shaft 354 lying to one side of the lumen and forming a boundary of the lumen, as shown in FIG. 19.

Figure 21:
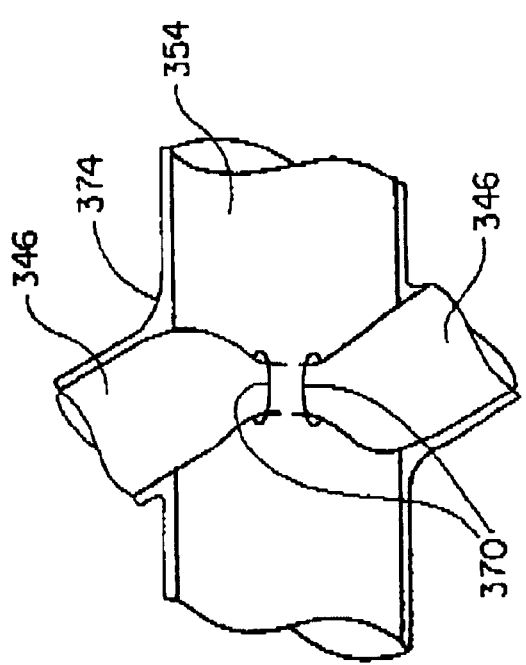
FIG. 21 is an enlarged fragmentary bottom view taken through line 21—21 in FIG. 16, illustrating an inflation coil laced through holes in the catheter shaft.

FIG. 19, illustrating a section taken through a complete inflation coil strand, shows the perfusion lumen created by the inflation of coil 346. Perfusion lumen 356 allows perfusing blood flow during radiation treatment. As illustrated by FIGS. 19, 20 and 21, distal shaft 354 has helix strand 346 secured by the lacing of strand 346 through through-holes 370. FIG. 21 illustrates in detail the securing of balloon strand 346 to shaft 354 using holes 370. In the embodiment shown, holes 70 form a pair aligned substantially transversely to the longitudinal axis of the shaft. In another embodiment, the through-holes can be oriented obliquely to the shaft longitudinal axis, substantially aligned with the helix strands as they approach the shaft. This later embodiment may not be self-securing and may require adhesive bonding to the shaft.

Lacing strand 346 repeatedly through shaft 354 removes shaft 354 to one side of perfusion lumen 356, creating a greater unobstructed area for perfusing blood flow, compared to placing shaft 354 within the center. Placing shaft 354 to one side by threading strand 346 through pairs of holes in the shaft brings an exterior portion of the shaft into fluid communication with the space between strands 346. As illustrated in FIG. 20, infusion holes 372, preferably located between strands 346, provide access from within infusion lumen 366 to the vessel wall the catheter is disposed within.

Infusion holes 372 and infusion lumen 366 can be used to infuse local agents in conjunction with radiation treatment. Infused substances can include agents to promote healing and agents to enhance the effect of radiation treatment. In particular, agents may be infused to prevent hypoxia (oxygen deprivation) while the balloon is inflated against vessel walls. Oxygenating agents include the patient's own arterial blood, which may be heparinized, and water or saline, which may be heparinized. Oxygenated blood, saline, water or other fluids can be used. Peroxides such as hydrogen peroxide can also be used to provide oxygen to vessel walls. Applicants believe the agents enhance the effectiveness of the radiation treatment.

Catheter 320 can also have a tubular sheath 374 disposed over strand 346 as illustrated in FIGS. 16 and 19. Sheath 374 is preferably formed of polyurethane elastomer. Sheath 374 is preferably configured to hug the contours of strand 346 such that inter-strand pockets 368 lie between the strands and also spiral around balloon assembly 336 as does strand 346. If sheath 374 lay straight between the outermost extent of strands 346, a substantially straight-walled cylindrical sheath would result, leaving less space between sheath and vessel wall for infusing drugs. As sheath 374 has inter-strand pockets 376, there is space for drugs to circulate and diffuse to contact the vessel walls. While a helical coil without a sheath provides some reduced flow, dead space for drug infusion near vessel walls, a sheath substantially insulates the vessel walls from perfusion flow and is the preferred embodiment.

Figure 22:
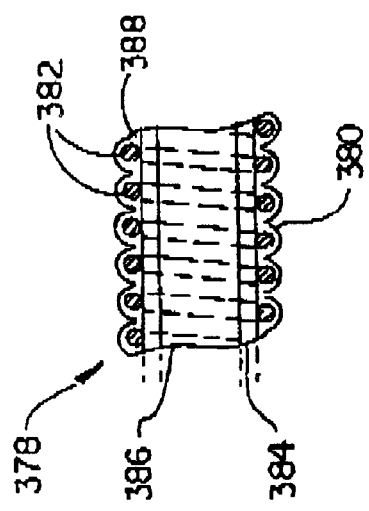
FIG. 22 is a fragmentary side view of a radiation wire member including a tube with radioactive coil.

Referring now to FIG. 22, a radiation wire device 378 having a distal region 380 is illustrated. A radioactive coil 382 is preferably wound about a radiation wire support tube 384 having a lumen 386. Support tube 384 is preferably formed of polyimide, having radioactive wire 382 wound around distal region 380 and covered with a shrink wrap layer 388 preferably formed of polyolefin copolymer.

In one embodiment, radiation wire support tube 384 is extremely flexible or floppy and incapable of being pushed alone through radiation wire lumen 360 from the catheter proximal end. In this embodiment, a radiation wire guide wire lumen 386 is included within tube 384, as illustrated in FIG. 22. A separate guide wire may be required for this embodiment, to guide the radiation emitting device through to the balloon assembly. A guide wire may be required to provide a pilot wire through the rise or bend 362 in the radiation wire tube, where the guide wire lumen enters the balloon assembly, where it may be difficult to push a flexible tube.

One embodiment includes perfusion holes proximal of coil 382, providing perfusion through lumen 386 when the guide wire is retracted. In this embodiment, the guide wire can be used to position the radiation member then retracted proximal of radiation wire tube rise 362, lessening the obstruction to perfusion blood flow during irradiation. The radiation member having perfusion holes is optimally used in conjunction with an open ended radiation tube, described below. Radiation wire coil 382 preferably includes Yttrium-90 or Nickel-66, high energy beta emitters. In another preferred embodiment, radiation wire 382 includes Gadolinium-153, a gamma emitter.

Figure 23:
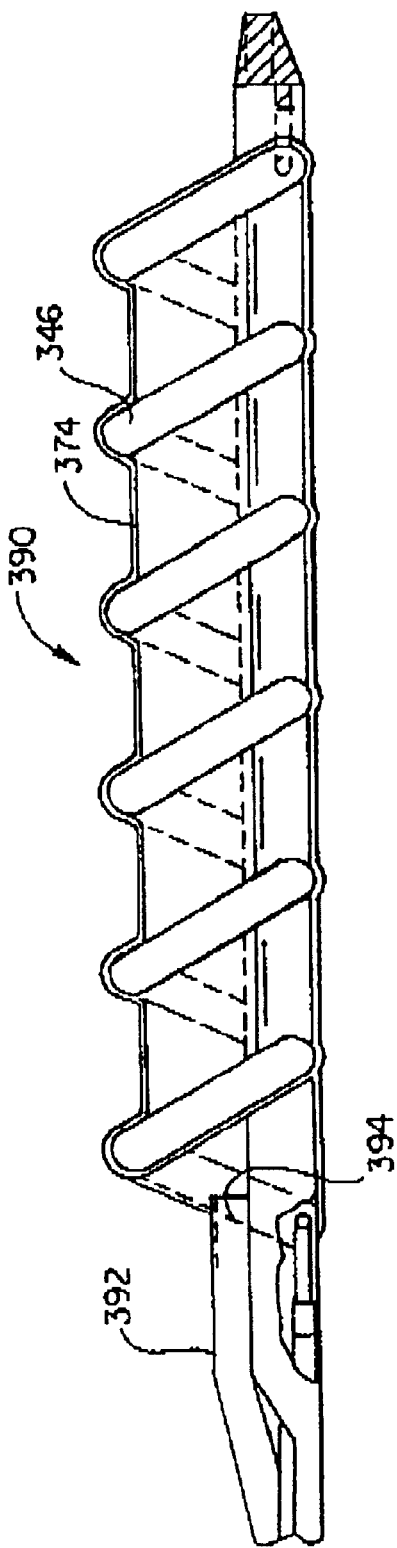
FIG. 23 is a fragmentary, side view of a catheter distal region having a radiation wire tube terminating proximate the proximal end of the inflation coil.

Referring now to FIG. 23, another embodiment catheter 390 is illustrated. Catheter 390 is similar to catheter 320, but has a radiation wire tube 392 with an open distal end 394. The resulting perfusion lumen 356 is still open to passage by the radiation wire, which can extend substantially through the balloon assembly, but without a supporting tube in this distal region. As can be visualized with FIG. 19, the removal of radiation wire tube 358 would provide greater cross sectional area for perfusing blood flow within perfusion lumen 356. The greater cross sectional area would be especially significant during periods when the radiation wire device itself is not within the perfusion lumen, as when the radiation wire device lies proximal of radiation wire tube bend 362. A device having no radiation wire tube within the inflatable balloon also provides a smaller profile for the balloon assembly in the deflated state, as can be illustrated by visualizing FIG. 19 without radiation wire tube 358. The open ended radiation wire lumen does allow contact between the radiation source and the bodily fluids. This may require sterilization or disposal of the radiation source after a single use.

As previously stated, a preferred source of radiation for all embodiments of the present invention is the radioactive compound Nickel-66. Nickel-66 decays with a half life of 2.28 days with only low energy beta emissions and no gamma emission into its daughter element Copper-66. Copper-66 then emits high energy beta radiation with a half life of 5.10 minutes and decays into the stabile element Zinc-66. This two-step decay has a particular advantage in use in the catheters of the present invention.

The Nickel-66 acts as a carrier for the high energy copper decay allowing for time to transport the source to the end user, and also allows for disposal of the device through ordinary means in about 23 days. A Copper-66 source alone would decay quickly and not be useful without the parent Nickel. Nickel is low cost and has desirable mechanical properties in its pure form and in alloys, such as a Nickel Titanium alloy.

The Nickel-66 can be utilized in any of the embodiments disclosed herein. Also, this source or another source could be incorporated into an atherectomy device. An exemplary embodiment of an atherectomy device is disclosed by Auth et al., in U.S. Pat. No. 5,314,407, the disclosure of which is incorporated herein by reference. A rotating ablative burr assembly is utilized to remove a stenosis. This burr assembly can have incorporated therein a radiation emitting source. Thus, radiation treatment can occur simultaneously with the atherectomy procedure.

Another preferred radiation source is Gadolinium-153. Gadolinium-153 is a composite gamma source which can provide low energy gammas to vessel intima layer while providing higher energy gammas to penetrate calcified plaques and reach the adventitia. Moderate shielding can be used with Gadolinium-153, allowing the treating physician to remain in the room with the patient during therapy. Another preferred source of radiation can include Yttrium-90, a high energy beta emitter.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. An intravascular radioactive radiation delivery catheter, comprising:
   an elongate shaft having a proximal portion, a distal portion and an inner tube having an inner lumen for the passage of a radioactive source therethrough;
   a helical centering balloon connected to the distal portion of the shaft; and
   a perfusion tube disposed on the distal end of the elongate shaft and through the helical balloon, the perfusion tube having a proximal perfusion port, a perfusion lumen and a distal perfusion port for the passage of blood therethrough.

2. An intravascular radioactive radiation delivery catheter as in claim 1, wherein the helical balloon includes helical windings that are closely adjacent when inflated.

3. An intravascular radioactive radiation delivery catheter as in claim 1, wherein the helical balloon includes helical windings that are in contact with adjacent windings when inflated.

4. An intravascular radioactive radiation delivery catheter as in claim 1, wherein the helical balloon includes helical windings, at least one winding including a reduced diameter portion for connection to the shaft.

5. An intravascular radioactive radiation delivery catheter as in claim 1, wherein a proximal end of the perfusion tube is connected to a distal end of the inner tube such that the inner lumen is connected to the perfusion lumen to collectively define a radioactive source lumen for the passage of the radioactive source therethrough.

6. An intravascular radioactive radiation delivery catheter as in claim 5, wherein the perfusion tube includes a distally facing opening.

7. An intravascular radioactive radiation delivery catheter as in claim 1, wherein the inner tube includes a flexible membrane to divide the inner lumen into a sterile portion and a non-sterile portion.

8. An intravascular radioactive radiation delivery catheter as in claim 1, wherein the shaft further includes a guide wire lumen having a proximal portion and a distal portion for the passage of a guide wire therethrough.

9. An intravascular radioactive radiation delivery catheter as in claim 8, wherein the distal portion of the guide wire lumen is common with the perfusion lumen.

10. An intravascular radioactive radiation delivery catheter as in claim 8, wherein the proximal portion of the guide wire lumen is common with the inner lumen.

11. An intravascular radioactive radiation delivery catheter as in claim 8, wherein the proximal portion of the guide wire lumen co-extends adjacent the inner lumen.

12. An intravascular radioactive radiation delivery catheter as in claim 8, wherein the proximal portion of the guide wire lumen terminates between the distal end of the shaft and the proximal end of the shaft.

13. An intravascular radioactive radiation delivery catheter as in claim 8, wherein the proximal portion of the guide wire lumen terminates adjacent the proximal end of the shaft.

14. An intravascular radioactive radiation delivery catheter, comprising:

an elongate shaft having a proximal portion, a distal portion, and an inner tube having an inner lumen;

a helical centering balloon connected to the distal portion of the shaft, the helical balloon having an interior for the passage of blood therethrough, the helical balloon also having an exterior; and a sheath disposed on the exterior of the helical centering balloon.

15. An intravascular radioactive radiation delivery catheter as in claim 14, wherein the helical balloon includes helical windings that are spaced apart when inflated.

16. An intravascular radioactive radiation delivery catheter as in claim 14, wherein the helical balloon includes helical windings, at least one winding including a reduced diameter portion for connection to the shaft.

17. An intravascular radioactive radiation delivery catheter as in claim 14, wherein the shaft further includes an infusion lumen having a proximal end and a distal end.

18. An intravascular radioactive radiation delivery catheter as in claim 17, wherein the distal end of the infusion lumen is in fluid communication with a space defined between the sheath and the vessel.

* * * * *